United States Patent
Carter et al.

(10) Patent No.: US 8,062,783 B2
(45) Date of Patent: Nov. 22, 2011

(54) SYSTEMS, DEVICES, AND METHODS FOR POWERING AND/OR CONTROLLING DEVICES, FOR INSTANCE TRANSDERMAL DELIVERY DEVICES

(75) Inventors: Darrick Carter, Seattle, WA (US);
Joshua K. Hoyt, Portland, OR (US);
James Thorne, Portland, OR (US);
Forrest Seitz, Beaverton, OR (US)

(73) Assignee: TTI ellebeau, Inc., Tokyo (JP)

( * ) Notice: Subject to any disclaimer, the term of this patent is extended or adjusted under 35 U.S.C. 154(b) by 673 days.

(21) Appl. No.: 11/947,667

(22) Filed: Nov. 29, 2007

(65) Prior Publication Data

US 2008/0154178 A1    Jun. 26, 2008

Related U.S. Application Data

(60) Provisional application No. 60/868,317, filed on Dec. 1, 2006, provisional application No. 60/949,810, filed on Jul. 13, 2007.

(51) Int. Cl.
*H01M 6/00* (2006.01)
*A61N 1/30* (2006.01)
*H01F 7/20* (2006.01)

(52) U.S. Cl. .................. 429/122; 604/20; 335/285

(58) Field of Classification Search ............ 429/122; 604/20; 335/285
See application file for complete search history.

(56) References Cited

U.S. PATENT DOCUMENTS

| | | | |
|---|---|---|---|
| 3,991,755 A | 11/1976 | Vernon et al. | 128/172.1 |
| 4,140,121 A | 2/1979 | Kühl et al. | 128/260 |
| 4,141,359 A | 2/1979 | Jacobsen et al. | 128/172.1 |
| 4,250,878 A | 2/1981 | Jacobsen et al. | 128/207.21 |
| 4,352,960 A | 10/1982 | Dormer et al. | |
| 4,406,658 A | 9/1983 | Lattin et al. | 604/20 |
| 4,474,570 A | 10/1984 | Ariura et al. | 604/20 |
| 4,585,652 A | 4/1986 | Miller et al. | 424/83 |
| 4,640,689 A | 2/1987 | Sibalis | 604/20 |
| 4,691,718 A | 9/1987 | Sakuma et al. | 132/84 |
| 4,702,732 A | 10/1987 | Powers et al. | 604/20 |
| 4,708,716 A | 11/1987 | Sibalis | 604/20 |
| 4,722,726 A | 2/1988 | Sanderson et al. | 604/20 |
| 4,725,263 A | 2/1988 | McNichols et al. | |
| 4,727,881 A | 3/1988 | Craighead et al. | 128/641 |
| 4,731,049 A | 3/1988 | Parsi | 604/20 |
| 4,744,787 A | 5/1988 | Phipps et al. | 604/20 |
| 4,747,819 A | 5/1988 | Phipps et al. | 604/20 |

(Continued)

FOREIGN PATENT DOCUMENTS

CA    2280046    8/1998

(Continued)

OTHER PUBLICATIONS

Kalia, Y., et al., "Iontophoretic Drug Delivery," *Advanced Drug Delivery Reviews*, 56:619-658, 2004.

(Continued)

*Primary Examiner* — Karie O'Neill Apicella
(74) *Attorney, Agent, or Firm* — Seed IP Law Group PLLC

(57) ABSTRACT

Systems, devices, and methods for powering and/or controlling electrically powered devices. A power supply system is operable to provide a voltage across at the active and the counter electrode assemblies of a transdermal delivery device. The system includes a power source and a magnetic coupling element.

17 Claims, 22 Drawing Sheets

U.S. PATENT DOCUMENTS

| | | | |
|---|---|---|---|
| 4,752,285 A | 6/1988 | Petelenz et al. | 604/20 |
| 4,764,164 A | 8/1988 | Sasaki | 604/20 |
| 4,786,277 A | 11/1988 | Powers et al. | 604/20 |
| 4,842,577 A | 6/1989 | Konno et al. | 604/20 |
| 4,915,685 A | 4/1990 | Petelenz et al. | 604/20 |
| 4,927,408 A | 5/1990 | Haak et al. | 604/20 |
| 4,931,046 A | 6/1990 | Newman | 604/20 |
| 4,940,456 A | 7/1990 | Sibalis et al. | 604/20 |
| 4,944,296 A | 7/1990 | Suyama | 128/393 |
| 5,006,108 A | 4/1991 | LaPrade | 604/20 |
| 5,047,007 A | 9/1991 | McNichols et al. | 604/20 |
| 5,084,006 A | 1/1992 | Lew et al. | 604/20 |
| 5,115,533 A | 5/1992 | Hukuba | 15/105 |
| 5,135,480 A | 8/1992 | Bannon et al. | 604/20 |
| 5,158,537 A | 10/1992 | Haak et al. | 604/20 |
| 5,162,043 A | 11/1992 | Lew et al. | 604/20 |
| 5,167,616 A | 12/1992 | Haak et al. | 604/20 |
| 5,167,785 A | 12/1992 | McCready | 204/196 |
| 5,203,768 A | 4/1993 | Haak et al. | 604/20 |
| 5,206,756 A | 4/1993 | Cheshire | 359/270 |
| 5,224,927 A | 7/1993 | Tapper | 604/20 |
| 5,224,928 A | 7/1993 | Sibalis et al. | 604/20 |
| 5,244,557 A | 9/1993 | Defendini et al. | 204/192.29 |
| 5,246,417 A | 9/1993 | Haak et al. | 604/20 |
| 5,246,418 A | 9/1993 | Haynes et al. | 604/20 |
| 5,254,081 A | 10/1993 | Maurer et al. | 604/20 |
| 5,284,471 A | 2/1994 | Sage, Jr. | 604/20 |
| 5,298,017 A | 3/1994 | Theeuwes et al. | 604/20 |
| 5,306,235 A | 4/1994 | Haynes | 604/20 |
| 5,310,404 A | 5/1994 | Gyory et al. | 604/20 |
| 5,312,326 A | 5/1994 | Myers et al. | 604/20 |
| 5,314,502 A | 5/1994 | McNichols et al. | 604/20 |
| 5,320,597 A | 6/1994 | Sage, Jr. et al. | 604/20 |
| 5,320,598 A | 6/1994 | Haak et al. | 604/20 |
| 5,322,502 A | 6/1994 | Theeuwes et al. | 604/20 |
| 5,322,520 A | 6/1994 | Milder | 604/265 |
| 5,326,341 A | 7/1994 | Lew et al. | 604/20 |
| 5,338,490 A | 8/1994 | Dietz et al. | 252/500 |
| 5,358,483 A | 10/1994 | Sibalis | 604/20 |
| 5,362,307 A | 11/1994 | Itoh et al. | 252/500 |
| 5,374,241 A | 12/1994 | Lloyd et al. | 604/20 |
| 5,380,271 A | 1/1995 | Gyory | 604/20 |
| 5,380,272 A | 1/1995 | Gross | 604/20 |
| 5,385,543 A | 1/1995 | Haak et al. | 604/20 |
| 5,405,317 A | 4/1995 | Myers et al. | 604/20 |
| 5,405,614 A | 4/1995 | D'Angelo et al. | 424/449 |
| 5,425,703 A | 6/1995 | Feiring | 604/21 |
| 5,445,606 A | 8/1995 | Haak et al. | 604/20 |
| 5,464,387 A | 11/1995 | Haak et al. | 604/20 |
| 5,511,548 A | 4/1996 | Riazzi et al. | 128/641 |
| 5,540,654 A | 7/1996 | Riviere et al. | 604/20 |
| 5,543,098 A | 8/1996 | Myers et al. | 264/104 |
| 5,551,953 A | 9/1996 | Lattin et al. | 604/20 |
| 5,558,633 A | 9/1996 | Phipps et al. | 604/20 |
| 5,573,503 A | 11/1996 | Untereker et al. | 604/20 |
| 5,582,587 A | 12/1996 | Gyory et al. | 604/20 |
| 5,605,536 A | 2/1997 | Sibalis | 604/20 |
| 5,618,265 A | 4/1997 | Myers et al. | 604/20 |
| 5,620,580 A | 4/1997 | Okabe et al. | 204/550 |
| 5,623,157 A | 4/1997 | Miyazaki et al. | 257/383 |
| 5,637,084 A | 6/1997 | Kontturi et al. | 604/20 |
| 5,645,526 A | 7/1997 | Flower | 604/20 |
| 5,646,815 A | 7/1997 | Owens et al. | 361/502 |
| 5,647,844 A | 7/1997 | Haak et al. | 604/20 |
| 5,660,178 A | 8/1997 | Kantner et al. | 128/640 |
| 5,685,837 A | 11/1997 | Horstmann | 604/20 |
| 5,688,232 A | 11/1997 | Flower | 604/20 |
| 5,723,130 A | 3/1998 | Hancock et al. | 424/211.1 |
| 5,725,817 A | 3/1998 | Milder | 264/104 |
| 5,730,716 A | 3/1998 | Beck et al. | 604/20 |
| 5,733,269 A | 3/1998 | Fuisz | 604/290 |
| 5,738,647 A | 4/1998 | Bernhard et al. | 604/20 |
| 5,746,711 A | 5/1998 | Sibalis et al. | 604/20 |
| 5,785,650 A | 7/1998 | Akasaka et al. | 600/300 |
| 5,795,321 A | 8/1998 | McArthur et al. | 604/20 |
| 5,800,685 A | 9/1998 | Perrault | 204/291 |
| 5,814,094 A | 9/1998 | Becker et al. | 607/50 |
| 5,817,044 A | 10/1998 | Evers et al. | 604/20 |
| 5,840,056 A | 11/1998 | Atanasoska | 604/20 |
| 5,919,155 A | 7/1999 | Lattin et al. | 604/20 |
| 5,928,185 A | 7/1999 | Muller et al. | 604/20 |
| 5,961,482 A | 10/1999 | Chien et al. | 604/20 |
| 5,976,101 A | 11/1999 | Sibalis | 604/20 |
| 5,991,655 A | 11/1999 | Gross et al. | 604/20 |
| 5,993,435 A | 11/1999 | Haak et al. | |
| 5,995,869 A | 11/1999 | Cormier et al. | 604/20 |
| 6,006,130 A | 12/1999 | Higo et al. | 604/20 |
| 6,009,345 A | 12/1999 | Hofmann | 604/20 |
| 6,032,073 A | 2/2000 | Effenhauser | 604/20 |
| 6,035,234 A | 3/2000 | Riddle et al. | 604/20 |
| 6,047,208 A | 4/2000 | Flower | 604/20 |
| 6,064,908 A | 5/2000 | Muller et al. | 604/20 |
| 6,086,572 A * | 7/2000 | Johnson et al. | 604/503 |
| 6,141,582 A | 10/2000 | Mori et al. | 604/20 |
| 6,163,720 A | 12/2000 | Gyory et al. | 604/20 |
| 6,167,302 A | 12/2000 | Millot | 604/20 |
| 6,169,920 B1 | 1/2001 | Haak et al. | 604/20 |
| 6,178,353 B1 | 1/2001 | Griffith et al. | 607/61 |
| 6,185,452 B1 | 2/2001 | Schulman et al. | 604/20 |
| 6,195,582 B1 | 2/2001 | Scott | 604/20 |
| 6,201,288 B1 | 3/2001 | Iwasaki et al. | 257/528 |
| 6,223,075 B1 | 4/2001 | Beck et al. | 604/20 |
| 6,228,206 B1 | 5/2001 | Herman et al. | 156/306.9 |
| 6,245,057 B1 | 6/2001 | Sieben et al. | 604/891.1 |
| 6,256,533 B1 | 7/2001 | Yuzhakov et al. | 604/21 |
| 6,289,241 B1 | 9/2001 | Phipps | 604/20 |
| 6,312,612 B1 | 11/2001 | Sherman et al. | 216/2 |
| 6,317,630 B1 | 11/2001 | Gross et al. | 604/20 |
| 6,327,496 B1 | 12/2001 | Hamlin et al. | 604/20 |
| 6,330,471 B1 | 12/2001 | Higo et al. | 604/20 |
| 6,334,856 B1 | 1/2002 | Allen et al. | 604/191 |
| 6,335,266 B1 | 1/2002 | Kitahara et al. | 438/475 |
| 6,336,049 B1 | 1/2002 | Kinbara et al. | 607/148 |
| 6,368,275 B1 | 4/2002 | Sliwa et al. | |
| 6,374,136 B1 | 4/2002 | Murdock | 604/20 |
| 6,377,847 B1 | 4/2002 | Keusch et al. | 604/20 |
| 6,377,848 B1 | 4/2002 | Garde et al. | 604/20 |
| 6,379,324 B1 | 4/2002 | Gartstein et al. | 604/22 |
| 6,385,488 B1 | 5/2002 | Flower et al. | 604/20 |
| 6,391,015 B1 | 5/2002 | Millot | 604/503 |
| 6,394,994 B1 | 5/2002 | Vilambi et al. | 604/501 |
| 6,402,732 B1 | 6/2002 | Flower et al. | 604/501 |
| 6,421,561 B1 | 7/2002 | Morris | 604/20 |
| 6,451,240 B1 | 9/2002 | Sherman et al. | 264/504 |
| 6,471,903 B2 | 10/2002 | Sherman et al. | 264/328.1 |
| 6,477,410 B1 | 11/2002 | Henley et al. | 604/20 |
| 6,496,727 B1 | 12/2002 | Bernhard et al. | 604/20 |
| 6,503,231 B1 | 1/2003 | Prausnitz et al. | 604/272 |
| 6,505,069 B2 | 1/2003 | Scott et al. | 604/20 |
| 6,511,463 B1 | 1/2003 | Wood et al. | 604/272 |
| 6,522,919 B1 | 2/2003 | Flower et al. | 604/20 |
| 6,532,386 B2 | 3/2003 | Sun et al. | 604/20 |
| 6,533,949 B1 | 3/2003 | Yeshurun et al. | 216/11 |
| 6,539,250 B1 | 3/2003 | Bettinger | |
| 6,553,253 B1 | 4/2003 | Chang | 604/20 |
| 6,553,255 B1 | 4/2003 | Miller et al. | 604/20 |
| 6,560,483 B1 | 5/2003 | Kumar et al. | 604/20 |
| 6,564,092 B1 | 5/2003 | Nakamura et al. | 604/20 |
| 6,565,532 B1 | 5/2003 | Yuzhakov et al. | 604/142 |
| 6,584,349 B1 | 6/2003 | Sage, Jr. et al. | 604/20 |
| 6,597,947 B1 | 7/2003 | Inoue et al. | 604/20 |
| 6,603,987 B2 | 8/2003 | Whitson | 600/345 |
| 6,611,707 B1 | 8/2003 | Prausnitz et al. | 604/21 |
| 6,635,045 B2 | 10/2003 | Keusch et al. | 604/501 |
| 6,653,014 B2 | 11/2003 | Anderson et al. | 429/122 |
| 6,654,635 B1 | 11/2003 | Koga et al. | 604/20 |
| 6,663,820 B2 | 12/2003 | Arias et al. | 264/496 |
| 6,678,554 B1 | 1/2004 | Sun et al. | 604/20 |
| 6,678,555 B2 | 1/2004 | Flower et al. | 604/20 |
| 6,692,456 B1 | 2/2004 | Eppstein et al. | 604/22 |
| 6,708,050 B2 | 3/2004 | Carim | 600/372 |
| 6,723,077 B2 | 4/2004 | Pickup et al. | 604/305 |
| 6,725,090 B1 | 4/2004 | Lattin et al. | 604/20 |
| 6,731,977 B2 | 5/2004 | Beck | 604/20 |
| 6,731,987 B1 | 5/2004 | McAdams et al. | 607/152 |
| 6,735,470 B2 | 5/2004 | Henley et al. | 604/20 |
| 6,743,015 B2 | 6/2004 | Magnani | 433/80 |

| Patent Number | Date | Inventor | Class |
|---|---|---|---|
| 6,743,432 B1 | 6/2004 | Yanai et al. | 424/400 |
| 6,745,071 B1 | 6/2004 | Anderson et al. | 604/20 |
| 6,767,341 B2 | 7/2004 | Cho | 604/272 |
| 6,775,569 B2 | 8/2004 | Mori et al. | 604/20 |
| 6,775,570 B2 | 8/2004 | Joshi | 604/20 |
| 6,790,372 B2 | 9/2004 | Roy et al. | 216/10 |
| 6,808,522 B2 | 10/2004 | Richards et al. | 604/890.1 |
| 6,815,360 B1 | 11/2004 | Canham et al. | 438/706 |
| 6,842,640 B2 | 1/2005 | Riddle et al. | 604/20 |
| 6,855,441 B1 | 2/2005 | Levanon | 429/7 |
| 6,862,473 B2 | 3/2005 | Keusch et al. | 604/20 |
| 6,881,203 B2 | 4/2005 | Delmore et al. | 604/272 |
| 6,908,453 B2 | 6/2005 | Fleming et al. | 604/173 |
| 6,915,159 B1 | 7/2005 | Kuribayashi et al. | 604/20 |
| 6,918,901 B1 | 7/2005 | Theeuwes et al. | 604/500 |
| 6,928,318 B2 | 8/2005 | Simon | 604/20 |
| 6,939,311 B2 | 9/2005 | Geiger | 600/573 |
| 6,975,902 B2 | 12/2005 | Phipps et al. | 604/20 |
| 6,994,933 B1 | 2/2006 | Bates | |
| 7,018,370 B2 | 3/2006 | Southam et al. | 604/501 |
| 7,033,598 B2 | 4/2006 | Lerner | 424/400 |
| 7,047,069 B2 | 5/2006 | Joshi | 604/20 |
| 7,054,682 B2 | 5/2006 | Young et al. | 604/20 |
| 7,103,578 B2 | 9/2006 | Beck et al. | 705/75 |
| 7,127,285 B2 | 10/2006 | Henley et al. | 604/20 |
| 7,280,873 B2 | 10/2007 | Freed et al. | 607/72 |
| 7,392,080 B2 | 6/2008 | Eppstein et al. | 604/20 |
| 7,797,041 B2 * | 9/2010 | Libbus et al. | 607/2 |
| 2001/0009983 A1 | 7/2001 | Walter et al. | 604/20 |
| 2001/0025246 A1 | 9/2001 | Haines et al. | 705/3 |
| 2002/0055704 A1 | 5/2002 | Scott et al. | 604/20 |
| 2002/0087193 A1 | 7/2002 | Riddle et al. | 607/2 |
| 2002/0099320 A1 | 7/2002 | Beck | 604/20 |
| 2002/0110739 A1 | 8/2002 | McEwen et al. | 429/324 |
| 2002/0123678 A1 | 9/2002 | Lerner et al. | 600/378 |
| 2002/0182485 A1 | 12/2002 | Anderson et al. | 429/105 |
| 2002/0188241 A1 | 12/2002 | Morris et al. | |
| 2003/0018295 A1 | 1/2003 | Henley et al. | 604/20 |
| 2003/0018296 A1 | 1/2003 | Riddle et al. | 604/20 |
| 2003/0028170 A1 | 2/2003 | Anderson et al. | 604/501 |
| 2003/0052015 A1 | 3/2003 | Becker et al. | 205/414 |
| 2003/0088204 A1 | 5/2003 | Joshi | 604/20 |
| 2003/0088205 A1 | 5/2003 | Chandrasekaran et al. | 604/20 |
| 2003/0135150 A1 | 7/2003 | Kuribayashi et al. | 604/20 |
| 2003/0167073 A1 | 9/2003 | Nakamura et al. | 607/2 |
| 2003/0181846 A1 | 9/2003 | Young et al. | 604/20 |
| 2003/0185023 A1 | 10/2003 | Hause, Jr. | 363/31 |
| 2003/0191426 A1 | 10/2003 | Lerner et al. | 604/20 |
| 2003/0195523 A1 | 10/2003 | Futsz | 606/117 |
| 2003/0199807 A1 | 10/2003 | Dent et al. | 604/20 |
| 2003/0199808 A1 | 10/2003 | Henley et al. | 604/20 |
| 2003/0208152 A1 | 11/2003 | Avrahami et al. | |
| 2003/0212397 A1 | 11/2003 | Avrahami et al. | 606/41 |
| 2004/0064084 A1 | 4/2004 | Inoue | 604/20 |
| 2004/0071765 A1 | 4/2004 | Adachi et al. | 424/449 |
| 2004/0082901 A1 | 4/2004 | Phipps et al. | 604/20 |
| 2004/0089533 A1 | 5/2004 | Hoagland et al. | 204/192.11 |
| 2004/0126323 A1 | 7/2004 | Shevchuk et al. | 424/10.1 |
| 2004/0138609 A1 | 7/2004 | Fukuta et al. | 604/20 |
| 2004/0143210 A1 | 7/2004 | Shevlin | 604/20 |
| 2004/0167804 A1 | 8/2004 | Simpson et al. | 705/3 |
| 2004/0176737 A1 | 9/2004 | Henley et al. | 604/501 |
| 2004/0176803 A1 | 9/2004 | Whelan et al. | 607/2 |
| 2004/0176805 A1 | 9/2004 | Whelan et al. | |
| 2004/0185667 A1 | 9/2004 | Jenson | 438/689 |
| 2004/0225253 A1 | 11/2004 | Shevlin | 604/20 |
| 2004/0248320 A1 | 12/2004 | Santini, Jr. et al. | 436/174 |
| 2004/0267169 A1 | 12/2004 | Sun et al. | 601/15 |
| 2004/0267232 A1 | 12/2004 | Sun et al. | 604/500 |
| 2004/0267236 A1 | 12/2004 | Sun et al. | 604/501 |
| 2004/0267240 A1 | 12/2004 | Gross et al. | 604/890.1 |
| 2005/0004506 A1 | 1/2005 | Gyory | 604/20 |
| 2005/0070840 A1 | 3/2005 | Matsumura et al. | 604/20 |
| 2005/0113744 A1 | 5/2005 | Donoghue et al. | 604/66 |
| 2005/0131336 A1 | 6/2005 | Mori et al. | 604/20 |
| 2005/0143686 A1 | 6/2005 | Shevlin | 604/20 |
| 2005/0148996 A1 | 7/2005 | Sun et al. | 604/501 |
| 2005/0169976 A1 | 8/2005 | Mori et al. | 424/449 |
| 2005/0187581 A1 | 8/2005 | Hara et al. | 607/2 |
| 2005/0192759 A1 | 9/2005 | Miyake et al. | 702/19 |
| 2005/0193554 A1 | 9/2005 | Young et al. | 29/825 |
| 2005/0203582 A1 | 9/2005 | Healy et al. | 607/31 |
| 2005/0215944 A1 | 9/2005 | Young et al. | 604/48 |
| 2005/0267440 A1 | 12/2005 | Herman et al. | 604/501 |
| 2005/0287201 A1 | 12/2005 | Till et al. | 424/450 |
| 2005/0288621 A1 | 12/2005 | Phipps et al. | 604/20 |
| 2006/0009730 A2 | 1/2006 | Shevlin | 604/20 |
| 2006/0024358 A1 | 2/2006 | Santini, Jr. et al. | 424/448 |
| 2006/0036209 A1 | 2/2006 | Subramony et al. | 604/20 |
| 2006/0043927 A1 | 3/2006 | Beart et al. | 320/108 |
| 2006/0052739 A1 | 3/2006 | Henley et al. | 604/20 |
| 2006/0095001 A1 | 5/2006 | Matsumura et al. | 604/20 |
| 2006/0116628 A1 | 6/2006 | Matsumura et al. | 604/20 |
| 2006/0129085 A1 | 6/2006 | Tanioka et al. | 604/20 |
| 2006/0135906 A1 | 6/2006 | Matsumura et al. | 604/20 |
| 2006/0173401 A1 | 8/2006 | Tanioka et al. | 604/20 |
| 2006/0217654 A1 | 9/2006 | Matsumura et al. | 604/20 |
| 2006/0235351 A1 | 10/2006 | Matsumura et al. | 604/20 |
| 2006/0247364 A1 | 11/2006 | Murray et al. | 524/495 |
| 2006/0258973 A1 | 11/2006 | Volt | 604/22 |
| 2006/0260955 A1 | 11/2006 | Sasaki et al. | 205/759 |
| 2006/0276742 A1 | 12/2006 | Matsumura et al. | 604/20 |
| 2007/0021711 A1 | 1/2007 | Matsumura et al. | 604/20 |
| 2007/0031730 A1 | 2/2007 | Kawakami et al. | 429/218.1 |
| 2007/0048362 A1 | 3/2007 | Nakayama et al. | 424/449 |
| 2007/0060859 A1 | 3/2007 | Kanamura et al. | 604/20 |
| 2007/0060860 A1 | 3/2007 | Nakayama et al. | 604/20 |
| 2007/0060862 A1 | 3/2007 | Sun et al. | 604/20 |
| 2007/0066930 A1 | 3/2007 | Tanioka et al. | 604/20 |
| 2007/0066931 A1 | 3/2007 | Kanamura et al. | 604/20 |
| 2007/0066932 A1 | 3/2007 | Akiyama et al. | 604/20 |
| 2007/0071807 A1 | 3/2007 | Akiyama et al. | 424/451 |
| 2007/0074590 A1 | 4/2007 | Smith | 73/866.1 |
| 2007/0078374 A1 | 4/2007 | Smith | 604/20 |
| 2007/0078375 A1 | 4/2007 | Smith | 604/20 |
| 2007/0078376 A1 | 4/2007 | Smith | 604/21 |
| 2007/0078445 A1 | 4/2007 | Malloy | 604/890.1 |
| 2007/0083176 A1 | 4/2007 | Carter et al. | 604/501 |
| 2007/0088331 A1 | 4/2007 | Nakayama et al. | 604/890.1 |
| 2007/0088332 A1 | 4/2007 | Akiyama et al. | 604/890.1 |
| 2007/0093787 A1 | 4/2007 | Smith | 604/890.1 |
| 2007/0093788 A1 | 4/2007 | Carter | 604/890.1 |
| 2007/0100274 A1 | 5/2007 | Young et al. | 604/20 |
| 2007/0112294 A1 | 5/2007 | Akiyama et al. | 604/20 |
| 2007/0135754 A1 | 6/2007 | Akiyama et al. | 604/20 |
| 2007/0139862 A1 | 6/2007 | Tateishi et al. | 361/502 |
| 2007/0196456 A1 | 8/2007 | Stevens et al. | 424/448 |
| 2007/0197955 A1 | 8/2007 | Akiyama et al. | 604/20 |
| 2007/0213652 A1 | 9/2007 | Carter | 604/20 |
| 2007/0232983 A1 | 10/2007 | Smith | 604/20 |
| 2008/0033338 A1 | 2/2008 | Smith | 604/20 |
| 2008/0033398 A1 | 2/2008 | Reed | 604/522 |
| 2008/0077076 A1 | 3/2008 | Carter | 604/20 |
| 2008/0114282 A1 | 5/2008 | Carter | 604/20 |
| 2008/0188791 A1 | 8/2008 | DiFore et al. | 604/20 |
| 2008/0214985 A1 | 9/2008 | Yanaki | 604/20 |
| 2008/0305154 A1 | 12/2008 | Yanaki | 424/449 |
| 2009/0146772 A1 | 6/2009 | Parsche et al. | |

FOREIGN PATENT DOCUMENTS

| | | |
|---|---|---|
| EP | 0 097 436 A1 | 1/1984 |
| EP | 0 357 852 A1 | 3/1990 |
| EP | 0 411 146 B1 | 2/1991 |
| EP | 0 504 715 A2 | 9/1992 |
| EP | 0 537 998 A1 | 4/1993 |
| EP | 0 547 482 A1 | 6/1993 |
| EP | 0 750 849 A1 | 1/1997 |
| EP | 0 813 879 B1 | 12/1997 |
| EP | 0 824 003 A2 | 2/1998 |
| EP | 0 904 779 B1 | 3/1999 |
| EP | 0 904 801 A2 | 3/1999 |
| EP | 0 931 564 A1 | 7/1999 |
| EP | 0 974 364 A1 | 1/2000 |
| EP | 1 440 707 A1 | 7/2004 |
| EP | 1 547 579 A1 | 6/2005 |
| EP | 1 566 197 A1 | 8/2005 |
| EP | 1 602 366 A1 | 12/2005 |
| EP | 1 712 579 A1 | 10/2006 |

| | | |
|---|---|---|
| FR | 2 787 729 A1 | 6/2000 |
| JP | 63-035266 | 2/1988 |
| JP | 7016518 | 3/1995 |
| JP | 7-504110 | 5/1995 |
| JP | 08-503875 | 4/1996 |
| JP | 09-201420 | 8/1997 |
| JP | 9-248344 | 9/1997 |
| JP | 2801083 | 7/1998 |
| JP | 11-19226 | 1/1999 |
| JP | 11-067236 | 3/1999 |
| JP | 11-076428 | 3/1999 |
| JP | 11-123246 | 5/1999 |
| JP | 11-158059 | 6/1999 |
| JP | 2901348 | 6/1999 |
| JP | 11-239621 | 9/1999 |
| JP | 3040517 B2 | 3/2000 |
| JP | 2000-229128 | 8/2000 |
| JP | 2000-229129 | 8/2000 |
| JP | 2000-237326 | 9/2000 |
| JP | 2000-237327 | 9/2000 |
| JP | 2000-237328 | 9/2000 |
| JP | 2000-237329 | 9/2000 |
| JP | 2000-288097 | 10/2000 |
| JP | 2000-288098 | 10/2000 |
| JP | 2000-316991 | 11/2000 |
| JP | 2001-070459 | 3/2001 |
| JP | 2001-120670 | 5/2001 |
| JP | 2001-523996 | 11/2001 |
| JP | 3290864 B2 | 6/2002 |
| JP | 2002-233584 | 8/2002 |
| JP | 2002-536133 | 10/2002 |
| JP | 2002-543942 | 12/2002 |
| JP | 2003-299743 | 10/2003 |
| JP | 2004-159673 | 6/2004 |
| JP | 2004-188188 | 7/2004 |
| JP | 2004-317317 | 10/2004 |
| JP | 2004-357313 | 12/2004 |
| JP | 2005-237755 | 9/2005 |
| JP | 2006-149891 | 6/2006 |
| JP | 2006-212194 | 8/2006 |
| JP | 2006-262943 | 10/2006 |
| JP | 2007-037639 | 2/2007 |
| JP | 2007-075327 | 3/2007 |
| WO | 91/16943 | 11/1991 |
| WO | 93/18727 | 9/1993 |
| WO | 94/22528 | 10/1994 |
| WO | 95/35132 | 12/1995 |
| WO | 96/10440 | 4/1996 |
| WO | 97/11744 | 4/1997 |
| WO | 97/48444 | 12/1997 |
| WO | 98/35722 | 8/1998 |
| WO | 9856458 | 12/1998 |
| WO | 99/38565 | 8/1999 |
| WO | 00/47274 | 8/2000 |
| WO | 00/53256 | 9/2000 |
| WO | 00/66216 | 11/2000 |
| WO | 01/39830 | 6/2001 |
| WO | 03/037425 | 5/2003 |
| WO | 03/061758 | 7/2003 |
| WO | 2004/017941 | 3/2004 |
| WO | 2004/028626 | 4/2004 |
| WO | 2004/070546 | 8/2004 |
| WO | 2005/120631 | 12/2005 |
| WO | 2006/046703 | 5/2006 |
| WO | 2006/055729 | 5/2006 |
| WO | 2007/010900 | 1/2007 |
| WO | 2007/017973 | 2/2007 |
| WO | 2007/018159 | 2/2007 |
| WO | 2007/023907 | 3/2007 |
| WO | 2007/026671 | 3/2007 |
| WO | 2007/029611 | 3/2007 |
| WO | 2007/032398 | 3/2007 |
| WO | 2007/032423 | 3/2007 |
| WO | 2007/037324 | 4/2007 |
| WO | 2007/037475 | 4/2007 |
| WO | 2007/037476 | 4/2007 |
| WO | 2007/066621 | 6/2007 |
| WO | 2007/099985 | 9/2007 |
| WO | 2007/111368 | 10/2007 |
| WO | 2008/027218 | 3/2008 |
| WO | 2008030497 A2 | 3/2008 |

OTHER PUBLICATIONS

Cabovska, "Investigations of Separation Mechanisms in Capillary Electrophoresis and High Performance Liquid Chromatography," Proquest, UMI No. 3120882, 2004.

Gomand, J. et al., "Impact of Permanent Magnet Field on Inductance Variation of a PMLSM," EPE 2007, 12th International Conference on Power Electronics and Applications, Aalborg, Denmark, Sep. 2-5, 2007, 9 pages.

Ning, N. et al., "Effect of External Magnetic Field on the Performance of Composite Wire Structured Magnetic Inductors," International Journal of Computer Applications in Technology 36(2):144-148, 2009, Abstract.

Saturation (magnetic), Wikipedia, URL=http://en.wikipedia.org/wiki/Saturation_(magnetic), download date Apr. 11, 2011, 3 pages.

Inductor Devices, Class Definition for Class 336, United States Patent and Trademark Office, URL=http://www.uspto.gov/web/patents/classification/uspc336/defs336.htm, download date Apr. 11, 2011, 8 pages.

* cited by examiner

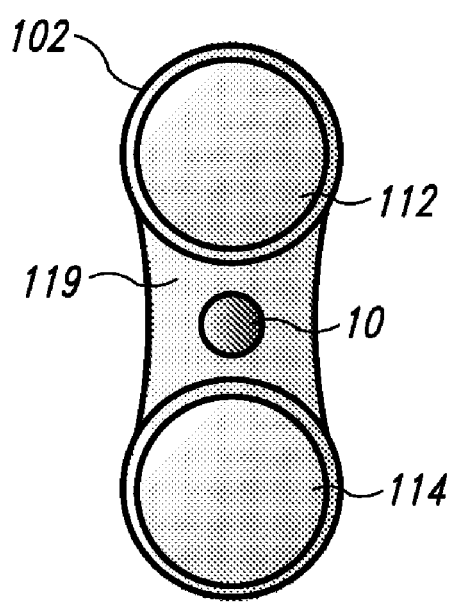
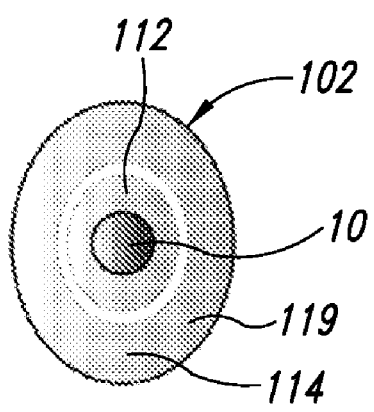
*FIG. 11*  *FIG. 12*

SYSTEMS, DEVICES, AND METHODS FOR POWERING AND/OR CONTROLLING DEVICES, FOR INSTANCE TRANSDERMAL DELIVERY DEVICES

CROSS-REFERENCE TO RELATED APPLICATIONS

This application claims the benefit under 35 U.S.C. §119(e) of U.S. Provisional Patent Application No. 60/868,317 filed Dec. 1, 2006; and U.S. Provisional Patent Application No. 60/949,810 filed Jul. 13, 2007; where the contents of these two provisional applications are incorporated herein by reference in their entireties.

BACKGROUND

1. Field

This disclosure generally relates to powering and/or controlling devices, for example medical devices, for instance transdermal delivery devices.

2. Description of the Related Art

Medical devices that employ electromotive forces are well known in the art. For example, iontophoretic drug delivery devices employ an electromotive force and/or current to transfer an active agent (e.g., a charged substance, an ionized compound, an ionic drug, a therapeutic, a bioactive-agent, and the like), to a biological interface (e.g., skin, mucus membrane, and the like), by using a small electrical charge applied to an iontophoretic chamber containing a similarly charged active agent and/or its vehicle.

Iontophoresis devices typically include an active electrode assembly and a counter electrode assembly, each coupled to opposite poles or terminals of a power source, for example a chemical battery or an external power station connected to the iontophoresis device via electrical leads. Each electrode assembly typically includes a respective electrode element to apply an electromotive force and/or current. Such electrode elements often comprise a sacrificial element or compound, for example silver or silver chloride. The active agent may be either cationic or anionic, and the power source may be configured to apply the appropriate voltage polarity based on the polarity of the active agent. Iontophoresis may be advantageously used to enhance or control the delivery rate of the active agent. The active agent may be stored in a reservoir such as a cavity. Alternatively, the active agent may be stored in a reservoir such as a porous structure or a gel. An ion exchange membrane may be positioned to serve as a polarity selective barrier between the active agent reservoir and the biological interface. The membrane, typically only permeable with respect to one particular type of ion (e.g., a charged active agent), prevents the back flux of oppositely charged ions from the skin or mucous membrane.

Commercial acceptance of iontophoresis devices is dependent on a variety of factors, such as cost to manufacture, shelf life, stability during storage, efficiency and/or timeliness of active agent delivery, biological capability, and/or disposal issues. Commercial acceptance of iontophoresis devices is also dependent on their versatility and ease-of-use. Therefore, it may be desirable to have novel approaches for powering iontophoresis devices.

The present disclosure is directed to overcoming one or more of the shortcomings set forth above, and providing further related advantages.

BRIEF SUMMARY

In one aspect, the present disclosure is directed to a portable power supply system for providing power to an electrically powered device. The portable power supply system includes a power source and a physical coupling structure for physically coupling the portable power supply system to the electrically powered device.

The portable power supply system may further include an electrical coupling structure for electrically coupling the portable power supply system to the electrical powered device.

In some embodiments, the electrical coupling structure is configured to electrically couple the portable power supply system to the electrically powered device in a correct electrical polarity, when the portable power supply system is physically coupled to the electrically powered device by the physical coupling structure.

In some further embodiments, the electrical coupling structure is configured to electrically couple the portable power supply system to the electrically powered device and inhibit electrical shorting of the electrical coupling structure, when the portable power supply system is physically coupled to the electrically powered device by the physical coupling structure.

In another aspect, the present disclosure is directed to a portable power supply system to provide power to an electrically powered device. The portable power supply system includes a power source and a first magnetic coupling element.

In some embodiments, the first magnetic coupling element is coupled to the power source and is magnetically-releasably attachable to the electrically powered device such that the power source is operable to provide electrical power to the electrically powered device, when the portable power supply system is magnetically coupled to the electrically powered device by the first magnetic coupling element.

In another aspect, the present disclosure is directed to a transdermal delivery device. The transdermal delivery device includes at least a first magnetic interconnect element and a control circuit. The transdermal delivery device further includes a substrate, a counter and an active electrode assembly, and a power supply.

The at least first magnetic interconnect element may magnetically-releasably couple the power supply to the substrate.

The counter electrode assembly includes at least one counter electrode element, and the active electrode assembly includes at least one active agent reservoir and at least one active electrode element. In some embodiments, the substrate carries the counter and active electrode assemblies.

The at least one active electrode element is operable to provide an electromotive force to drive an active agent from the at least one active agent reservoir to a biological interface of a subject. In some embodiments, the control circuit electrically couples to provide a voltage across the counter and the active electrode elements from a power source carried by the power supply during at least a portion of a period when the power supply is magnetically-releasably coupled to the substrate.

In another aspect, the present disclosure is directed to an encapsulated battery assembly for powering a transdermal delivery device. The encapsulated battery assembly includes a housing, a power source, and a control circuit.

The housing has an exterior surface and an interior surface, the interior surface defining an isolated space. The power source is received in the isolated space of the housing. In some embodiments, the encapsulated battery assembly includes means for transferring power to at least one electrode of the transdermal delivery device from the power source, when the encapsulated battery assembly is releasably coupled to the transdermal delivery device.

The control circuit is received in the isolated space of the housing and operable to control a voltage and a current of the power delivered to the at least one electrode assembly of the transdermal delivery device.

In another aspect, the present disclosure is directed to an iontophoretic drug delivery system for providing transdermal delivery of one or more active agents to a biological interface of a subject. The iontophoretic drug delivery system includes a counter electrode assembly, an active electrode assembly, a flexible circuit, and a printed power source.

The active electrode assembly includes at least one active agent reservoir, and is operable to provide an electromotive force to drive at least some of the at least one active agent from the at least one active reservoir to the biological interface. The flexible circuit is electrically coupleable to the counter and active electrode assemblies, and is operable to control an electromotive force supplied to the active electrode assembly. The printed power source is electrically coupled to the flexible circuit, and is operable to supply an electromotive force to the active electrode assembly.

In yet another aspect, the present disclosure is directed to a detachable controller for a transdermal drug delivery device including a substrate. The substrate includes a control circuit, a power source, and one or more coupling elements. The power source is electrically coupleable to the control circuit. In some embodiments, the one or more coupling elements physically couple the detachable controller to the transdermal drug delivery device.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements, as drawn, are not intended to convey any information regarding the actual shape of the particular elements, and have been solely selected for ease of recognition in the drawings.

FIG. 11 is a top plan view of a transdermal delivery device comprising an active electrode assembly and a counter electrode assembly according to one illustrated embodiment.

FIG. 12 is a top plan view of a transdermal delivery device comprising an active electrode assembly and a counter electrode assembly according to another illustrated embodiment.

DETAILED DESCRIPTION

Figure 1A:
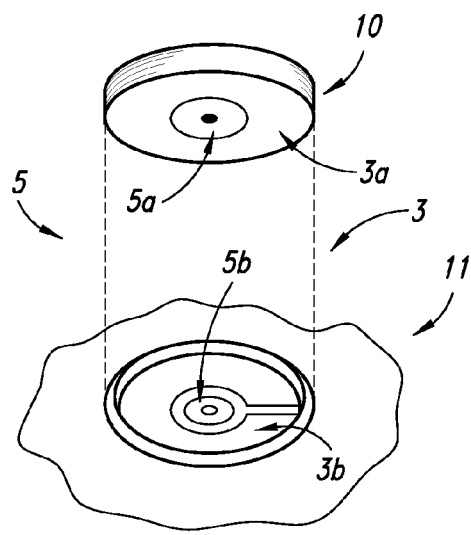
FIG. 1A is an isometric view of a portable power supply system and an electrically powered device according to one illustrated embodiment.

In the following description, certain specific details are included to provide a thorough understanding of various disclosed embodiments. One skilled in the relevant art, however, will recognize that embodiments may be practiced without one or more of these specific details, or with other methods, components, materials, etc. In other instances, well-known structures associated with electrically powered devices including but not limited to voltage and/or current regulators have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," or "an embodiment," or "in another embodiment" means that a particular referent feature, structure, or characteristic described in connection with the embodiment is included in at least one embodiment. Thus, the appearance of the phrases "in one embodiment," or "in an embodiment," or "in another embodiment" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. Thus, for example, reference to an electrically powered device including "a power source" includes a single power source, or two or more power sources. It should also be noted that the term "or" is generally employed in its sense including "and/or" unless the content clearly dictates otherwise.

As used herein the term "membrane" means a boundary, layer, barrier, or material, which may or may not be permeable. The term "membrane" may further refer to an interface. Unless specified otherwise, membranes may take the form of a solid, a liquid, or a gel, and may or may not have a distinct lattice, non-cross-linked structure, or cross-linked structure.

As used herein the term "ion selective membrane" means a membrane that is substantially selective to ions, passing certain ions while blocking passage of other ions. An ion selective membrane, for example, may take the form of a charge selective membrane, or may take the form of a semi-permeable membrane.

As used herein the term "charge selective membrane" means a membrane that substantially passes and/or substantially blocks ions based primarily on the polarity or charge carried by the ion. Charge selective membranes are typically referred to as ion exchange membranes, and these terms are used interchangeably herein and in the claims. Charge selective or ion exchange membranes may take the form of a cation exchange membrane, an anion exchange membrane, and/or a bipolar membrane. A cation exchange membrane substantially permits the passage of cations and substantially blocks anions. Examples of commercially available cation exchange membranes include those available under the designators NEOSEPTA, CM-1, CM-2, CMX, CMS, and CMB from Tokuyama Co., Ltd. Conversely, an anion exchange membrane substantially permits the passage of anions and substantially blocks cations. Examples of commercially available anion exchange membranes include those available under the designators NEOSEPTA, AM-1, AM-3, AMX, AHA, ACH, and ACS, also from Tokuyama Co., Ltd.

As used herein and in the claims, the term "bipolar membrane" means a membrane that is selective to two different charges or polarities. Unless specified otherwise, a bipolar membrane may take the form of a unitary membrane structure, a multiple membrane structure, or a laminate. The unitary membrane structure may include a first portion including cation ion exchange materials or groups and a second portion opposed to the first portion, including anion ion exchange materials or groups. The multiple membrane structure (e.g., two-film structure) may include a cation exchange membrane laminated or otherwise coupled to an anion exchange membrane. The cation and anion exchange membranes initially start as distinct structures, and may or may not retain their distinctiveness in the structure of the resulting bipolar membrane.

As used herein and in the claims, the term "semi-permeable membrane" means a membrane that is substantially selective based on a size or molecular weight of the ion. Thus, a semi-permeable membrane substantially passes ions of a first molecular weight or size, while substantially blocking passage of ions of a second molecular weight or size, greater than the first molecular weight or size. In some embodiments, a semi-permeable membrane may permit the passage of some molecules at a first rate, and some other molecules at a second rate different from the first. In yet further embodiments, the "semi-permeable membrane" may take the form of a selectively permeable membrane allowing only certain selective molecules to pass through it.

As used herein and in the claims, the term "porous membrane" means a membrane that is not substantially selective with respect to ions at issue. For example, a porous membrane is one that is not substantially selective based on polarity, and not substantially selective based on the molecular weight or size of a subject element or compound.

As used herein and in the claims, the term "gel matrix" means a type of reservoir, which takes the form of a three-dimensional network, a colloidal suspension of a liquid in a solid, a semi-solid, a cross-linked gel, a non-cross-linked gel, a jelly-like state, and the like. In some embodiments, the gel matrix may result from a three-dimensional network of entangled macromolecules (e.g., cylindrical micelles). In some embodiments, a gel matrix may include hydrogels, organogels, and the like. Hydrogels refer to three-dimensional network of, for example, cross-linked hydrophilic polymers in the form of a gel and substantially composed of water. Hydrogels may have a net positive or negative charge, or may be neutral.

As used herein and in the claims, the term "reservoir" means any form of mechanism to retain an element, compound, pharmaceutical composition, active agent, and the like, in a liquid state, solid state, gaseous state, mixed state and/or transitional state. For example, unless specified otherwise, a reservoir may include one or more cavities formed by a structure, and may include one or more ion exchange membranes, semi-permeable membranes, porous membranes and/or gels if such are capable of at least temporarily retaining an element or compound. Typically, a reservoir serves to retain a biologically active agent prior to the discharge of such agent by electromotive force and/or current into the biological interface. A reservoir may also retain an electrolyte solution.

As used herein and in the claims, the term "active agent" refers to a compound, molecule, or treatment that elicits a biological response from any host, animal, vertebrate, or invertebrate, including, for example, fish, mammals, amphibians, reptiles, birds, and humans. Examples of active agents include therapeutic agents, pharmaceutical agents, pharmaceuticals (e.g., a drug, a therapeutic compound, pharmaceutical salts, and the like) non-pharmaceuticals (e.g., a cosmetic substance, and the like), a vaccine, an immunological agent, a local or general anesthetic or painkiller, an antigen or a protein or peptide such as insulin, a chemotherapy agent, and an anti-tumor agent.

In some embodiments, the term "active agent" refers to the active agent as well as to its pharmacologically active salts, pharmaceutically acceptable salts, prodrugs, metabolites, analogs, and the like. In some further embodiments, the active agent includes at least one ionic, cationic, ionizeable, and/or neutral therapeutic drug, and/or pharmaceutically acceptable salts thereof. In yet other embodiments, the active agent may include one or more "cationic active agents" that are positively charged, and/or are capable of forming positive charges in aqueous media. For example, many biologically active agents have functional groups that are readily convertible to a positive ion or can dissociate into a positively charged ion and a counter ion in an aqueous medium. Other active agents may be polarized or polarizable, that is exhibiting a polarity at one portion relative to another portion. For instance, an active agent having an amino group can typically take the form an ammonium salt in solid state and dissociates into a free ammonium ion ($NH4^+$) in an aqueous medium of appropriate pH.

The term "active agent" may also refer to electrically neutral agents, molecules, or compounds capable of being delivered via electro-osmotic flow. The electrically neutral agents are typically carried by the flow of, for example, a solvent during electrophoresis. Selection of the suitable active agents is therefore within the knowledge of one skilled in the relevant art.

In some embodiments, one or more active agents may be selected from analgesics, anesthetics, anesthetics vaccines, antibiotics, adjuvants, immunological adjuvants, immunogens, tolerogens, allergens, toll-like receptor agonists, toll-like receptor antagonists, immuno-adjuvants, immuno-modulators, immuno-response agents, immuno-stimulators, specific immuno-stimulators, non-specific immuno-stimulators, and immuno-suppressants, or combinations thereof.

Non-limiting examples of such active agents include lidocaine, articaine, and others of the -caine class; morphine, hydromorphone, fentanyl, oxycodone, hydrocodone, buprenorphine, methadone, and similar opioid agonists; sumatriptan succinate, zolmitriptan, naratriptan HCl, rizatriptan benzoate, almotriptan malate, frovatriptan succinate and other 5-hydroxytryptaminel receptor subtype agonists; resiquimod, imiquidmod, and similar TLR 7 and 8 agonists and antagonists; domperidone, granisetron hydrochloride, ondansetron and such anti-emetic drugs; zolpidem tartrate and similar sleep inducing agents; L-dopa and other anti-Parkinson's medications; aripiprazole, olanzapine, quetiapine, risperidone, clozapine, and ziprasidone, as well as other neuroleptica; diabetes drugs such as exenatide; as well as peptides and proteins for treatment of obesity and other maladies.

Further non-limiting examples of active agents include ambucaine, amethocaine, isobutyl p-aminobenzoate, amolanone, amoxecaine, amylocalne, aptocaine, azacaine, bencaine, benoxinate, benzocaine, N,N-dimethylalanylbenzocaine, N,N-dimethylglycylbenzocaine, glycylbenzocaine, beta-adrenoceptor antagonists betoxycaine, bumecaine, bupivicaine, levobupivicaine, butacaine, butamben, butanilicaine, butethamine, butoxycaine, metabutoxycaine, carbizocaine, carticaine, centbucridine, cepacaine, cetacaine, chloroprocaine, cocaethylene, cocaine, pseudococaine, cyclomethycaine, dibucaine, dimethisoquin, dimethocaine, diperodon, dyclonine, ecognine, ecogonidine, ethyl aminobenzoate, etidocaine, euprocin, fenalcomine, fomocaine, heptacaine, hexacaine, hexocaine, hexylcaine, ketocaine, leucinocaine, levoxadrol, lignocaine, lotucaine, marcaine, mepivacaine, metacaine, methyl chloride, myrtecaine, naepaine, octacaine, orthocaine, oxethazaine, parenthoxycaine, pentacaine, phenacine, phenol, piperocaine, piridocaine, polidocanol, polycaine, prilocalne, pramoxine, procaine (NOVOCAINE®), hydroxyprocaine, propanocaine, proparacaine, propipocaine, propoxycaine, pyrrocaine, quatacaine, rhinocaine, risocaine, rodocaine, ropivacaine, salicyl alcohol, tetracaine, hydroxytetracaine, tolycaine, trapencaine, tricaine, trimecaine tropacocaine, zolamine, a pharmaceutically acceptable salt thereof, and mixtures thereof.

As used herein and in the claims, the term "subject" generally refers to any host, animal, vertebrate, or invertebrate, and includes fish, mammals, amphibians, reptiles, birds, and particularly humans.

As used herein and in the claims, the term "agonist" refers to a compound that can combine with a receptor (e.g., an opioid receptor, toll-like receptor, and the like) to produce a cellular response. An agonist may be a ligand that directly binds to the receptor. Alternatively, an agonist may combine with a receptor indirectly by forming a complex with another molecule that directly binds the receptor, or otherwise results in the modification of a compound so that it directly binds to the receptor.

As used herein and in the claims, the term "antagonist" refers to a compound that can combine with a receptor (e.g., an opioid receptor, a toll-like receptor, and the like) to inhibit a cellular response. An antagonist may be a ligand that directly binds to the receptor. Alternatively, an antagonist may combine with a receptor indirectly by forming a complex with another molecule that directly binds to the receptor, or otherwise results in the modification of a compound so that it directly binds to the receptor.

As used herein and in the claims, the term "effective amount" or "therapeutically effective amount" includes an amount effective at dosages and for periods of time necessary, to achieve the desired result. The effective amount of a composition containing a pharmaceutical agent may vary according to factors such as the disease state, age, gender, and weight of the subject.

As used herein and in the claims, the term "analgesic" refers to an agent that lessens, alleviates, reduces, relieves, or extinguishes a neural sensation in an area of a subject's body. In some embodiments, the neural sensation relates to pain, in other aspects the neural sensation relates to discomfort, itching, burning, irritation, tingling, "crawling," tension, temperature fluctuations (such as fever), inflammation, aching, or other neural sensations.

As used herein and in the claims, the term "anesthetic" refers to an agent that produces a reversible loss of sensation in an area of a subject's body.

In some embodiments, the anesthetic is considered to be a "local anesthetic" in that it produces a loss of sensation only in one particular area of a subject's body.

As one skilled in the relevant art would recognize, some agents may act as both an analgesic and an anesthetic, depending on the circumstances and other variables including but not limited to dosage, method of delivery, medical condition or treatment, and an individual subject's genetic makeup. Additionally, agents that are typically used for other purposes may possess local anesthetic or membrane stabilizing properties under certain circumstances or under particular conditions.

As used herein and in the claims, the term "immunogen" refers to any agent that elicits an immune response. Examples of an immunogen include but are not limited to natural or synthetic (including modified) peptides, proteins, lipids, oligonucleotides (RNA, DNA, etc.), chemicals, or other agents.

As used herein and in the claims, the term "allergen" refers to any agent that elicits an allergic response. Some examples of allergens include but are not limited to chemicals and plants, drugs (such as antibiotics, serums), foods (such as milk, wheat, eggs, etc), bacteria, viruses, other parasites, inhalants (dust, pollen, perfume, smoke), and/or physical agents (heat, light, friction, radiation). As used herein, an allergen may be an immunogen.

As used herein and in the claims, the term "adjuvant" and any derivation thereof refers to an agent that modifies the effect of another agent while having few, if any, direct effects when given by itself. For example, an adjuvant may increase the potency or efficacy of a pharmaceutical, or an adjuvant may alter or affect an immune response.

As used herein and in the claims, the term "opioid" generally refers to any agent that binds to and/or interacts with opioid receptors. Among the opioid classes examples include endogenous opioid peptides, opium alkaloids (e.g., morphine, codeine, and the like), semi-synthetic opioids (e.g., heroin, oxycodone and the like), synthetic opioids (e.g., buprenorphinemeperidine, fentanyl, morphinan, benzomorphan derivatives, and the like), as well as opioids that have structures unrelated to the opium alkaloids (e.g., pethidine, methadone, and the like).

As used herein and in the claims, the terms "vehicle," "carrier," "pharmaceutical vehicle," "pharmaceutical carrier," "pharmaceutically acceptable vehicle," or "pharmaceutically acceptable carrier" may be used interchangeably, and refer to pharmaceutically acceptable solid or liquid, diluting or encapsulating, filling or carrying agents, which are usually employed in the pharmaceutical industry for making pharmaceutical compositions. Examples of vehicles include any liquid, gel, salve, cream, solvent, diluent, fluid ointment base, vesicle, liposome, nisome, ethasomes, transfersome, virosome, non-ionic surfactant vesicle, phospholipid surfactant vesicle, micelle, and the like, that is suitable for use in contacting a subject.

In some embodiments, the pharmaceutical vehicle may refer to a composition that includes and/or delivers a pharmacologically active agent, but is generally considered to be otherwise pharmacologically inactive. In some other embodiments, the pharmaceutical vehicle may have some therapeutic effect when applied to a site such as a mucous membrane or skin, by providing, for example, protection to the site of application from conditions such as injury, further injury, or exposure to elements. Accordingly, in some embodiments, the pharmaceutical vehicle may be used for protection without a pharmacological agent in the formulation.

The headings provided herein are for convenience only and do not interpret the scope or meaning of the embodiments.

Figure 1B:
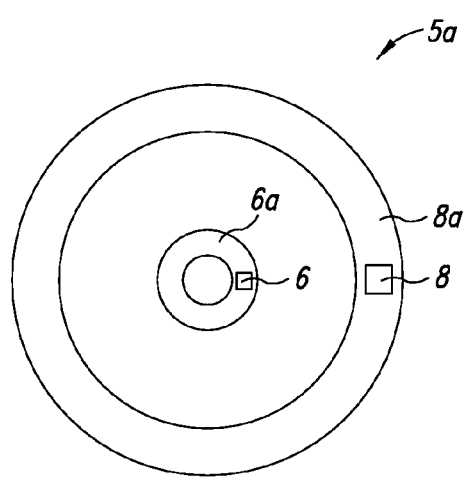
FIG. 1B is a bottom plan view of a portion of a power coupling structure of a portable power supply system according to one illustrated embodiment.
Figure 1C:
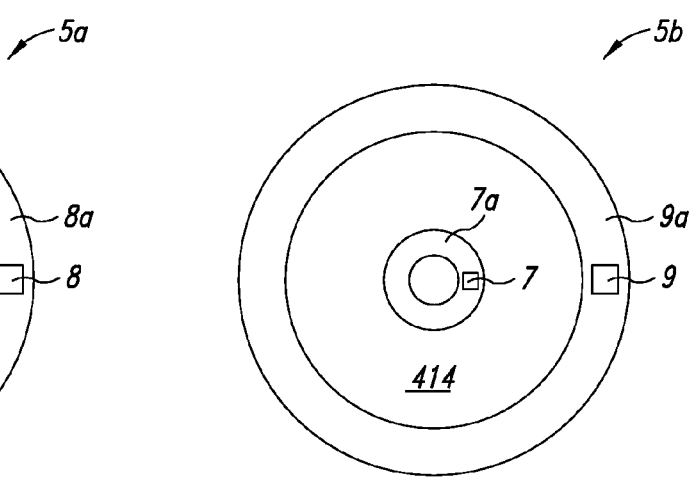
FIG. 1C is a top plan view of a portion of a power coupling structure of an electrically powered device according to one illustrated embodiment.
Figure 2:
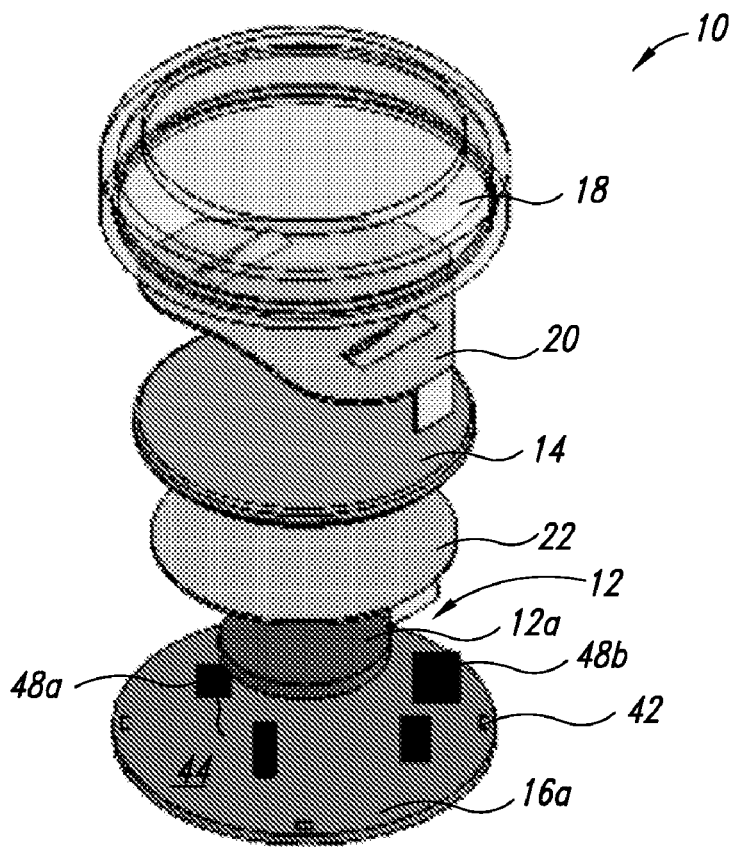
FIG. 2 is an exploded view of a portable power supply system according to one illustrated embodiment.
Figure 3:
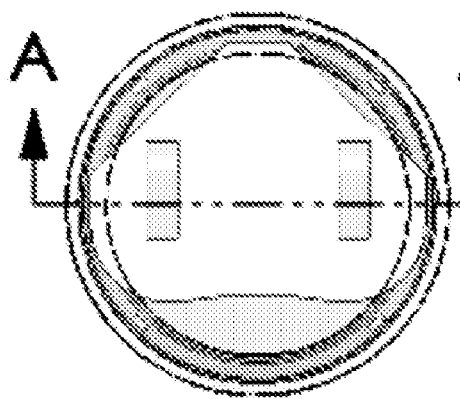
FIG. 3 is a top plan view of the portable power supply system of FIG. 2 according to one illustrated embodiment.
Figure 4:
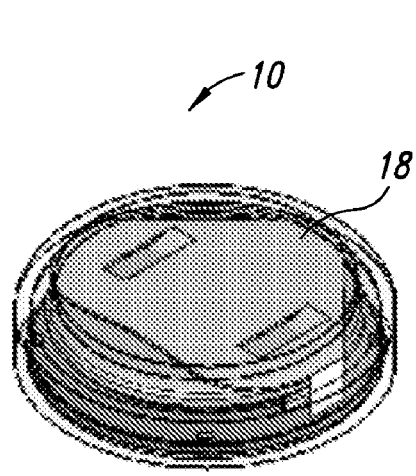
FIG. 4 is a top front isometric view of the portable power supply system of FIG. 2 according to one illustrated embodiment.

FIGS. 1A, 1B, and 1C show an exemplary portable power supply system 10 for providing power to an electrically powered device 11 (e.g., an iontophoretic delivery device, a transdermal patch, an active agent delivery device, and the like).

The portable power supply system 10 may include one or more physical coupling structures 3 for physically coupling the portable power supply system 10 to the electrically powered device 11.

The one or more physical coupling structures 3 may take a variety of forms. In some embodiments, the physical coupling structure may include one or more distinct elements 3a, 3b. For example, the physical coupling structure may include one or more couplers, fasteners, connectors, inter-connectors, polarized connectors, hook and loop type fasteners, snap-fitting type fasteners, snap type fasteners, friction fit type fasteners, detent elements, magnetic couplers, magnetic connectors, and the like. In particularly advantageous embodiments, the physical coupling structures 3 may take the form of a magnetic physical coupling structure 12. As explained in more detail below, such magnetic physical coupling structure 12 may include a number of distinct elements, for instance, one or more permanent magnets, one or more ferrous, ferromagnetic, or ferrimagnetic elements or coatings and/or one or more electromagnets.

In some embodiments, the portable power supply system 10 may be permanently physically coupled (i.e., directly or indirectly) to the electrically powered device 11. In other embodiments, the portable power supply system 10 may be releasably physically coupled to the electrically powered device 11 via one or more physical coupling structures 3. In both the permanently physically coupled embodiments and the releasably physically coupled embodiments, the portable power supply system 10 is also coupled to provide power to the electrically powered device 11 via one or more power coupling structures 5, for example, via electrical, inductive and/or capacitive coupling.

In some embodiments, the portable power supply system 10 and the electrically powered device 11 may include one or more power coupling structures for electrically, inductive, and/or capacitive coupling the portable power supply system 10 to the electrically powered device 11.

The one or more power coupling structures 5 may take a variety of forms. In some embodiments, the power coupling structures 5 may include one or more distinct elements 5a, 5b. For example, the power coupling structures 5 may include one or more contacts, leads, terminals, inductors, or plates, which are or may be positioned with respect to one another to effectively transfer power between the portable power supply system 10 and the electrically powered device 11. Such transfer of power may be, for example, electrically or conductively, inductively or capacitively.

In some embodiments, the power coupling structure 5 may take the form of one or more electrical coupling structures 5a, 5b, for electrically coupling the portable power supply system 10 to the electrically powered device 11. Among the electrical coupling structures 5a, 5b examples include one or more contacts, leads, terminals, inductors, plates, polarized coupling elements, multi-pin connectors, DIN connectors, polarized multi-pin connectors, circular connectors, slot type interconnectors, and the like, which are or may be positioned with respect to one another to effectively transfer power between the portable power supply system 10 and the electrically powered device 11.

The one or more electrical coupling structures 5a of the portable power supply system 10 are configured to electrically couple to the corresponding one or more electrical coupling structures 5b of the electrically powered device 11 in correct electrical polarity. For example, in some embodiments, the one or more power coupling structures 5 may take the form of polarized (configured to provide corresponding electrical polarity coupling elements) power coupling elements that prevent incorrect or reversed power coupling of the portable power supply system 10 to the electrically powered device 11.

As shown FIGS. 1B and 1C, in some embodiments, one or more electrical coupling structures 6, 8 of the portable power supply system 10 are configured to electrically couple to the corresponding one or more electrical coupling structures 7,9 of the electrically powered device 11 with no electrical shorting between the electrical coupling structures 6,8 of the portable power supply system 10 and the electrical coupling structures 7,9 of the electrically powered device 11. In some embodiments, the spacing between the electrical contacts 6, 8 of the portable power supply system 10, as well as the spacing between the electrical contacts 7, 9 of the electrically powered device 11 precludes shorting when the portable power supply system 10 is physically coupled to the electrically powered device 11 by the physical coupling structure 3.

In some embodiments, the one or more physical coupling structures 3 are configured to retain the portable power supply system 10 in a position and/or orientation that ensures a correct polarity between power (e.g., electrical, inductive or capacitive) coupling structures 5a (e.g., contacts, terminals or leads and the like) of the portable power supply system 10 and power coupling structures 5b of the electrically powered device 11.

In some further embodiments, an electrical coupling structure 6 of a first polarity of the portable power supply system 10 is configured to electrically couple to the corresponding power coupling structure 7 of the first polarity of the electrically powered device 11, and an electrical coupling structure 8 of a second polarity, opposite to the first polarity, of the portable power supply system 10 is configured to electrically couple to the corresponding electrical coupling structure 9 of the second polarity of the electrically powered device 11, with no electrical shorting. For example, in some embodiments, the power coupling structures 6,8 and 7,9 take the form of two or more electrical contacts 6a, 8a and 7a, 9a respectively, each respectively forming a concentric geometric pattern that provides universally oriented proper electrical polarity alignment of the electrical contacts 6a, 8a and 7a, 9a.

Additionally, the concentric pattern form by, for example, electrical contacts 6a, 8a, as well as by electrical contacts 7a, 9a, creates an enhanced "target" message for a user coupling the portable power supply system 10 to the electrically powered device 11.

FIGS. 2 through 5B show an exemplary portable power supply system 10 for providing power to the electrically powered device 11.

In some embodiments, the portable power supply system 10 includes a coupling element 12 configured to physical couple the portable power supply system 10 to the electrically powered device 11, and a power source 14. The portable power supply system 10 may further include a circuit 16. In some embodiments, the power supply system 10 includes at least one of a cover 18, a power source holder 20, and a power source contact 22.

In some embodiments, the coupling element 12 is magnetically-releasably attachable to the electrically powered device 11. In some embodiments, the coupling element 12 takes the form of a first magnetic coupling element 12a coupled to the power source 14. The first magnetic coupling element 12a is magnetically-releasably attachable to the electrically powered device 11 such that the power source 14 is operable to provide electrical power to the electrically powered device 11 in response to the portable power supply system 10 being magnetically coupled to the electrically powered device 11 by the first magnetic coupling element 12a.

Examples of a suitable first magnetic coupling element 12a include permanent magnets, one or more ferrous, ferromagnetic, or ferrimagnetic elements or coatings and/or one or more electromagnets. In some embodiments, a suitable first magnetic coupling element 12a includes at least one of a paramagnetic material element, a ferromagnetic material element, ferromagnetic coatings (e.g., ferrous paint), magnetic coatings (e.g., magnetic paint), and the like.

Paramagnetic materials (e.g., aluminum, copper, lithium, magnesium, molybdenum, platinum, tantalum, and the like) typically have a small and positive susceptibility (a relative magnetic permeability greater than unity) to magnetic fields and are attracted to a magnetic field (e.g., a magnet). Ferromagnetic materials (e.g., cobalt, iron, nickel, gadolinium, steel, and the like) typically have a large and positive susceptibility to magnetic fields and are attracted to a magnetic field.

In some embodiments, the first coupling element 12a may take the form of at least one ferrous metal element. The ferrous metal element may, in some embodiments, magnetically-releasably attach the portable power supply system 10 to a magnet (e.g., a permanent magnet, and the like) carried by the electrically powered device 11.

In some other embodiments, the first magnetic coupling element 12a takes the form of at least one permanent magnet. The at least one permanent magnet may, in some embodiments, magnetically-releasably attach the portable power supply system 10 to a paramagnetic material element, a ferromagnetic material element, and the like, carried by the electrically powered device 11.

Examples of the at least one permanent magnet include high-energy flexible magnets, neodymium magnets, ceramic magnets, samarium cobalt magnets, alnico magnets, rare earth magnets, and the like. In some embodiments, the first magnetic coupling element 12a may further be electrically conductive and electrically coupleable to a first pole of the power source 14. In some embodiments, the second magnetic coupling element may further be electrically conductive and electrically coupleable to a second pole of the power source 14

The portable power supply system 10 may further include a second magnetic coupling element physically coupled to the power source 14. In some embodiments, the second magnetic coupling element is operable to releasably attach the portable power supply system 10 to the electrically powered device 11.

In some embodiments, the second magnetic coupling element may further be electrically conductive and electrically coupleable to a second pole of the power source 14. In such embodiments, the second magnetic coupling element is configured to releasably retain the portable power supply system 10 in a correct electrical polarity with respect to the electrically powered device 11. In some embodiments, the second magnetic coupling element has a magnetic polarity opposite a magnetic polarity of the first magnetic coupling element 12*a*. Examples of a suitable second magnetic coupling element 12*a* include permanent magnets, one or more ferrous, ferromagnetic, or ferrimagnetic elements or coatings and/or one or more electromagnets. In some embodiments, a suitable second magnetic coupling element 12*a* includes at least one of a paramagnetic material element, a ferromagnetic material element, ferromagnetic coatings (e.g., ferrous paint), magnetic coatings (e.g., magnetic paint), and the like.

The power source 14 is operable to provide electrical power to power the electrically powered device 11 in response to the portable power supply system 10 being coupled to the electrically powered device 11. Examples of the electrically powered device 11 include medical devices, transdermal delivery devices (e.g., iontophoretic delivery devices), and the like. In some embodiments, the power source 14 takes the form of at least one chemical battery cell, an ultra-capacitor, a fuel, and the like. In some embodiments, the power source 14 takes the form of at least one primary cell or secondary cell. Other suitable examples of power source 14 include at least one of a button cell, a coin cell, an alkaline cell, a lithium cell, a lithium ion cell, a zinc air cell, a nickel metal hydride cell, and the like. In some embodiments, the power source 14 takes the form of at least one printed battery, energy cell laminate, thin-film battery, power paper, and the like, or combinations thereof.

In some embodiments, the portable power supply system 10 may releasably attach and/or releasably coupled to the electrically powered device 11 using, for example, a physical coupling structure. In some embodiments, the physical coupling structure may include a ferrous paint element releasably attachable and/or releasably coupled to a magnetic substrate. In some embodiments, the physical coupling structure may include a ferrous substrate releasably attachable and/or releasably coupled to a magnetic substrate. In some embodiments, the physical coupling structure may include a ferrous substrate releasably attachable and/or releasably coupled to a magnetic paint element. In some embodiments, the physical coupling structure may include a ferrous paint element releasably attachable and/or releasably coupled to a magnetic paint element. In some embodiments, the physical coupling structure may include a hook and loop fastener physical coupling structure. In some embodiments, the physical coupling structure may include a multi-part EKG/ECG type interconnect using, for example, concentrically patterned fasteners. In yet some other embodiments, the physical coupling structure may include a slot type physical coupling structure.

Figure 5A:
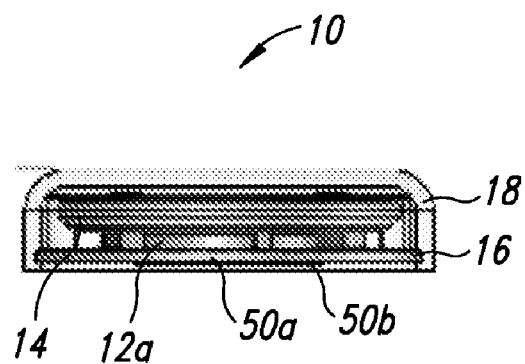
FIG. 5A is a cross-sectional view of a site taken along the line A-A of the portable power supply system of FIG. 3 according to one illustrated embodiment.
Figure 5B:
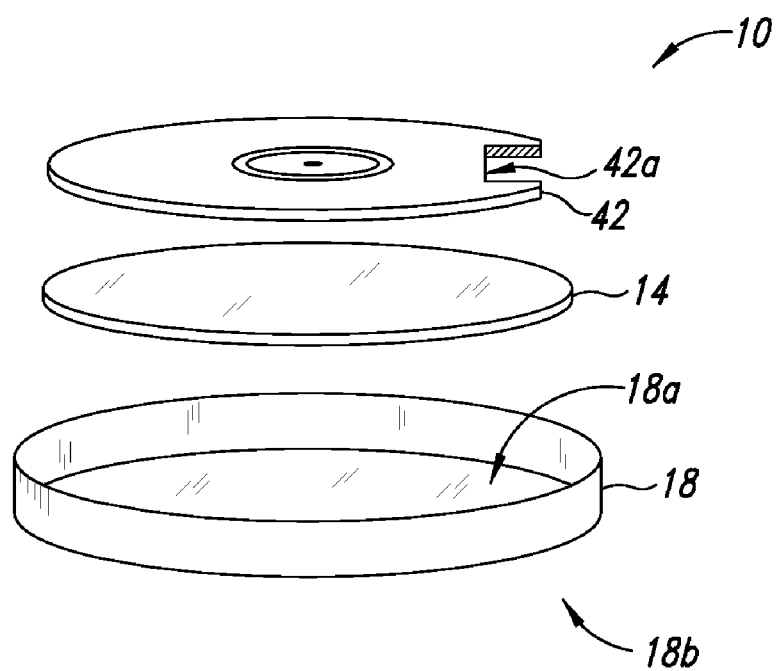
FIG. 5B is a top front isometric view of the portable power supply system including a replaceable battery according to one illustrated embodiment.

As shown in FIG. 5B, in some embodiments, the portable power supply system 10 may include a replaceable power source 14. In some embodiments, substrate 42 may be detachably affixed to the cover 18 such that the substrate 42 is movable between an open position (as shown in FIG. 5B) and a close position (as shown in FIG. 5A). In the opened position, the interior 18*a* of the cover 18 may be accessible from the exterior 18*b* of the cover 18, allowing for the placement, removal, or replacement of the power source 14. In the closed position, there may be limited access to the interior of the cover 18.

In some embodiments, the substrate 42 may be detachably affixed to the cover 18 using one or more couplers, fasteners, friction-fit structures, thread-coupled structures, bayonet-coupled structures, and the like. For example, the substrate 42 may be thread-coupled to the cover 18. In some embodiments, substrate 42 can be detached from to the cover 18 to allow for the placement, removal, or replacement of the power source 14. For example, substrate 42 may be disengaged from the cover 18 allowing for the placement, removal, or replacement of the power source 14 carried within. In some embodiments, substrate 42 may include a notch 42 structure to facilitate the prying or disengaging of substrate 42 from the cover 18 and allowing for the placement, removal, or replacement of the power source 14. In some embodiments, substrate 42 may include a tab structure to facilitate the prying or disengaging of substrate 42 from the cover 18 and allowing for the placement, removal, or replacement of the power source 14.

Figure 6:
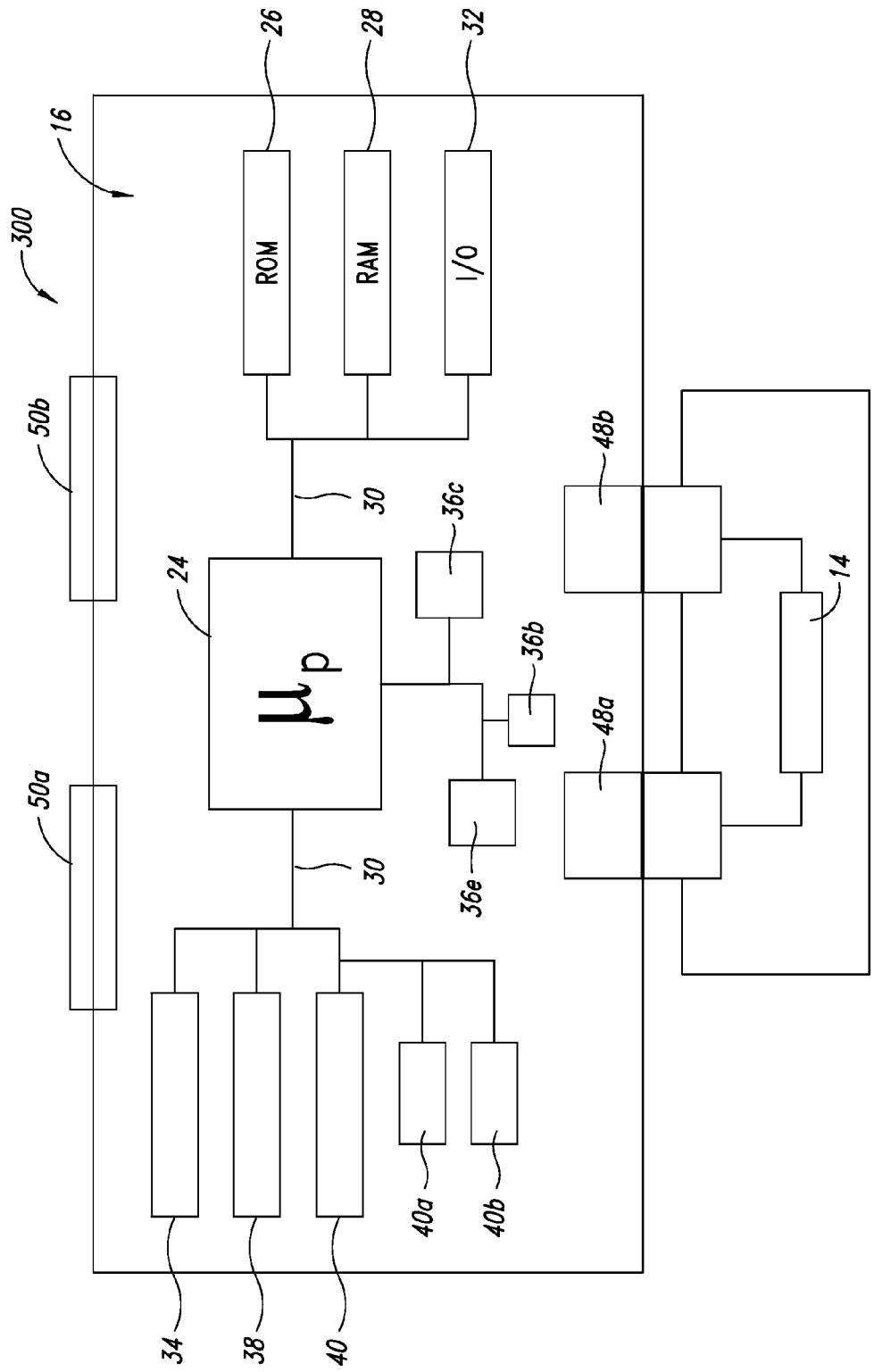
FIG. 6 is a functional block diagram showing a portable power supply system according to one illustrative embodiment.
Figure 7:
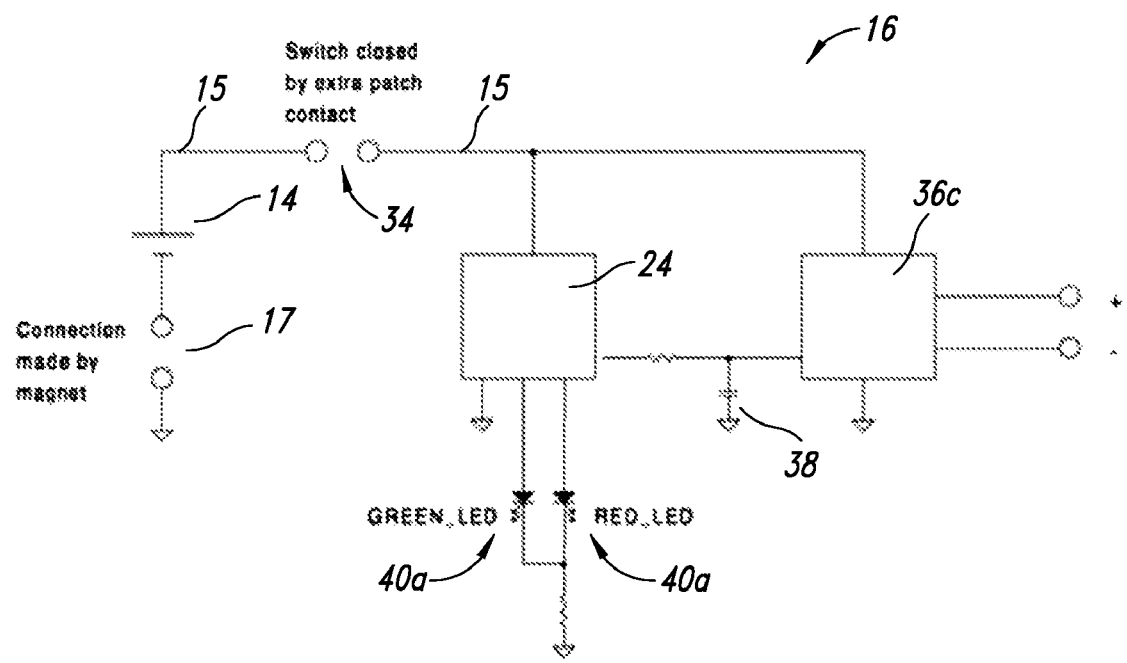
FIG. 7 is a schematic diagram of a circuit for a portable power supply system according to one illustrative embodiment.

As shown in FIGS. 6 and 7, the portable power supply system 10 may also include a control system in the form of a control circuit 16 to control the voltage, current, and/or power delivered to the electrically powered device 11. The control circuit 16 may include one or more controllers 24 such as a microprocessor, a digital signal processor (DSP) (not shown), an application-specific integrated circuit (ASIC) (not shown), and the like. The control circuit 16 may also include one or more memories, for example, read-only memory (ROM) 26, random access memory (RAM) 28, and the like, coupled to the controllers 24 by one or more busses 30. The control circuit 16 may further include one or more input devices 32 (e.g., a display, touch-screen display, and the like).

The control circuit 16 may also include discrete and/or integrated circuit elements 36*a*, 36*b*, 36*c* to control the voltage, current, and/or power. For example, the control circuit 16 may include a diode to provide a constant current to the electrically powered device 11. In some embodiments, the control circuit 16 may include a rectifying circuit element to provide a direct current voltage and/or a voltage/current regulator. In other embodiments, the control circuit 16 sinks and sources voltage to maintain a steady state operation of the electrically powered device 11. The control circuit 16 may be electrically coupled to receive current from the power source 14, via electrical contacts 15. In some embodiments, the control circuit 16 may take the form of a programmable control circuit operable to provide at least a first current profile. In some embodiments, the control circuit 16 may take the form of a programmable control circuit operable to provide a plurality of current profiles. For example, the control circuit 16 may be operable to provide at least a first current profile associated with the control delivery, sustained delivery, and the like, associated with transdermal delivery of one or more active agents to a biological interface of a subject.

In some embodiments, the control circuit 16 is configured to track, store, transmit, receive, and/or retrieve treatment management data. For example, the control circuit 16 may be configured to track, store, transmit, receive, and/or retrieve transdermal delivery device information. In some embodiments, the control circuit 16 may be configured to query tag data (e.g., a Radio Frequency Identification (RFID) tag) including for example stored data codes, user data, patient data, drug delivery device data, and the like.

In some embodiments, the control circuit 16 is configured to store and/or track historical data, use data, patient data, and the like. In some embodiments, the control circuit 16 includes an RFID type chip to store, track, receive, and retrieve delivery device (e.g., iontophoretic delivery device, transdermal patch, and the like) information, query tag data, store data codes, track use data, track patient data, and the like. The RFID type chip may take the form of, for example, an active type RFID type chip, receiving power form the portable power supply system 10. In some embodiments, the RFID type chip may take the form of a passive type RFID type chip using, for example, only a memory portion of RFID type chip. In some embodiments, a portion of the RFID type chip is used for memory without using the RF capabilities of the RFID type chip. Such may advantageously take advantage of low cost chips produced for high volume applications such as RFID.

As shown in FIG. 7, in some embodiments, the control circuit 16 is configured to automatically close (e.g., via circuit element 17) in response to the portable power supply system 10 being releasably attached to the electrically powered device 11. The control circuit 16 may include a switch 34 selectively operable to control a supply of current to the electrically powered device 11 in response to the portable power supply system 10 being releasably attached to the electrically powered device 11. In some embodiments, the switch 34 is selectively operable to automatically close in response to the portable power supply system 10 being releasably attached to the electrically powered device 11. In some embodiments, the control circuit 16 may further include self-test capabilities that are initiated once the control circuit 16 is closed.

The control circuit 16 may further include a start and/or stop switch 38 for selectively controlling the flow of current to the control circuit 16. The switch 38 may take the form of a dome switch, a membrane switch, a tactile switch, a single-use dome switch, a single-use membrane switch, a single-use tactile switch, and the like.

In some embodiments, the control circuit 16 may be operable to detect a power source polarity and provide a charge of a proper polarity to respective ones of a positive electrical contact and a negative electrical contact of the electrically powered device, in response to the portable power supply system 10 being releasably attached to the electrically powered device 11.

The portable power supply system 10 may further include one or more indicators 40 to, for example, alert a user that the portable power supply system 10 is operating properly. Examples of the one or more indicators 40 include visual feedback elements 40a (e.g., light-emitting diodes (LEDs)) (e.g., green LEDs and red LEDs), a display, and the like), audio feedback elements 40b (e.g., an alarm), and the like.

In some embodiments, the portable power supply system 10 has a largest dimension of less than about 25 mm, and a smallest dimension of less than about 10 mm. In some embodiments, the portable power supply system 10 has an aspect ratio ranging from about 2:1 to about 13:1.

Figure 8:
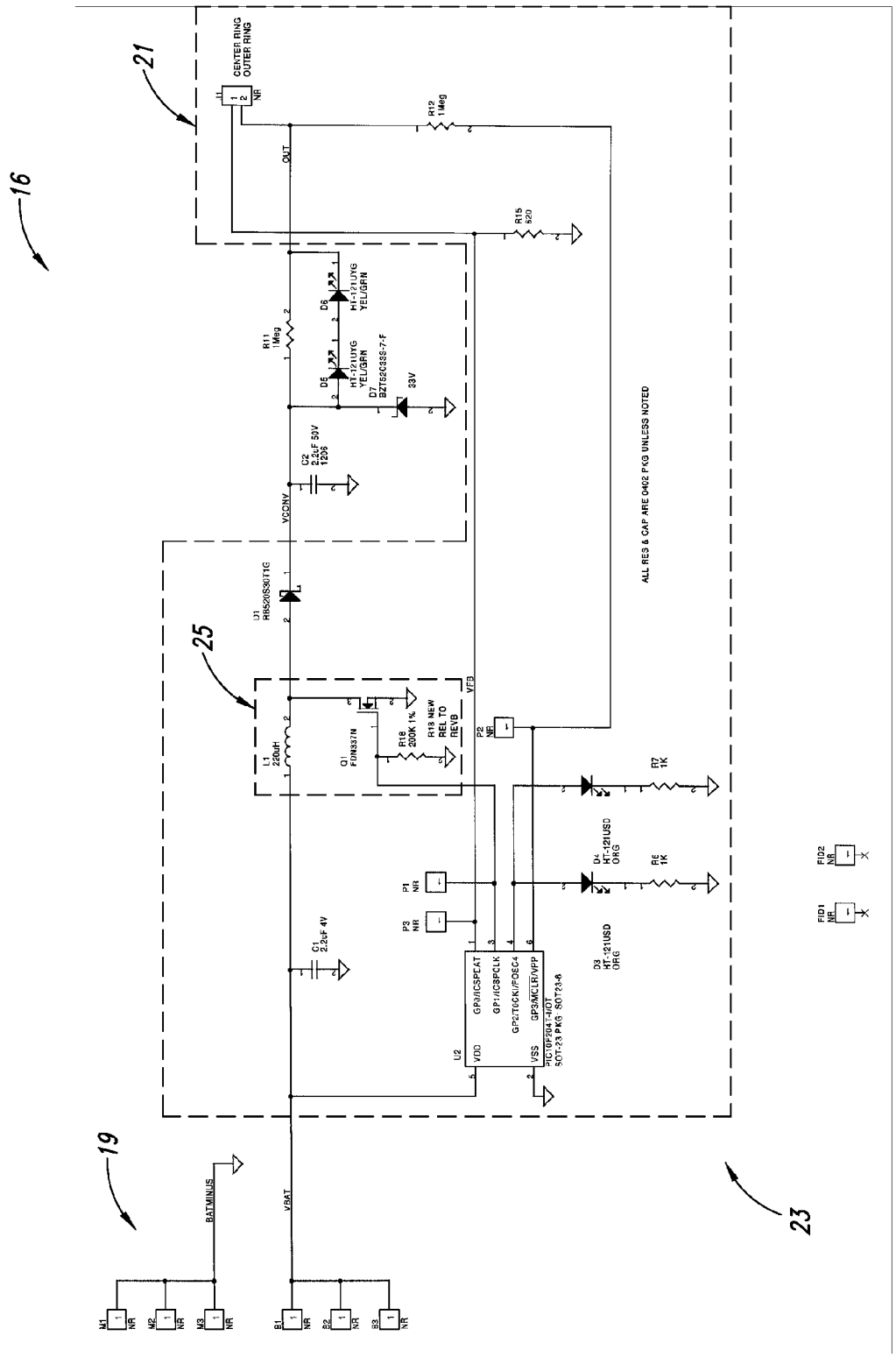
FIG. 8 is a schematic diagram of a control circuit according to one illustrative embodiment.

FIG. 8 shows a control circuit 16, according to one illustrated embodiment.

The control circuit 16 includes a number of input terminals 19, a number of output terminals 21, a regulation circuit 23 coupled between the input and output terminals 19, 21, a number of indicators D3-D6, and a controller U2.

The input terminals 19 provide a structure to electrically couple the control circuit 16 to a power source, for example a chemical battery cell. As illustrated, the control circuit 16 may include three input terminals B1-B3 of a first polarity and three input terminals M1-M3 of a second polarity. Such may ensure good electrical contact with the power source 14, although some embodiments may employ a lesser or greater number of input terminals.

The output terminals 21 provide a structure to supply electrical power to electrodes of an active agent delivery device, for example an iontophoresis patch. As noted previously, the output terminals 21 may comprise a first and a second terminal, one for each polarity. The output terminals 21 may be configured, shaped, and/or arranged to assure that the correct polarity is maintained when coupling, for example, the portable power supply system 10 to the electrically powered device 11. For example, the output terminals 21 may be formed as two concentric structures, for example, an inner pad and an outer annulus or ring surrounding the inner pad. In some embodiments, the inner pad may take the form of an annulus or ring shape, however other shapes are possible. Further, in some embodiments, the other structure may be a shape other than an annulus or ring. In some embodiments, one of the output terminals 21 may substantially or completely surround in the other output terminal 21, while in other embodiments, one of the output terminals 21 may only partially surround or may not even partially surround the other input terminal 19.

The regulation circuit 23 includes a power converter 25 operable to adjust or maintain a current and/or voltage at the output terminals 21, for example, as discussed in detail below. The power converter 25 may take the form of current regulator, boost converter, buck converter, or some combination of the same. As illustrated, the regulation circuit 23 may take the form of a boost converter formed, for example, by an inductor L1 coupled between the input and output terminals of a switch Q1 operable to selectively couple the inductor L1 to ground. In the embodiment illustrated in FIG. 8, the switch Q1 may take the form of a transistor having a gate, a drain, and a source.

The control circuit 16 may include a Schottky diode D1 to prevent damage in the event of a reversal of polarity. The control circuit 16 may include a Zener diode D7 coupled to ground to prevent output voltage from exceeding a desired level. The control circuit 16 may also include an input capacitor C1 coupled to ground, between the output terminals 21 and the inductor L1 to act as an input filter. The control circuit 16 may further include an output capacitor C2 coupled to ground, between the inductor L1 and the output terminals 21 to act as an output filter, reducing ripple in the output current.

The controller U2 may take a variety of forms, for example a microcontroller, processor, microprocessor, digital signal processor, field programmable gate array, or the like. The controller U2 includes power and ground connectors or pins VDD, VSS. The controller U2 supplies drive signals to the gate of the transistor Q1 via output or pin 3 of the controller U2. Inputs or pins 1, 6 of the controller U2 are coupled to terminals 1,2 of the output terminals 21, respectively. Thus, the controller U2 can determine or sense the operating characteristics at the output terminals 21. For example, the controller U2 may be responsive to the presence or absence of a load across the output terminals 21 via a load sense resistor R12. The value of R12 may be selected such that the impedance associated with skin or other biological tissue (e.g., 20 K Ohms) is sufficient to trigger the controller U2. The controller U2 may also be responsive to a measure of voltage across and/or flow of current at the output terminals 21. For example, in the illustrated embodiment the controller U2 is responsive to a measure of current via a current sense resistor R15.

The controller U2 may be normally powered and/or in the ON state, and may be programmed or otherwise configured to perform certain functions upon detection or in response to a load across the output terminals 21 via load sense resistor R12. For example, the controller U2 may be configured or programmed to perform one or more tests, provide appropriate indications, and/or take appropriate actions based on the results of the tests, and/or start delivery active agent according to one or more delivery profiles. For example, the controller U2 may enter a test or startup mode upon detection of a load, and may enter a current supply mode upon successful completion of the test and startup mode. The controller U2 may be in a wait or sleep mode prior to detecting a load, for example, while the portable power supply system 10 is in storage. An energy efficient controller U2 may be stored for many years while monitoring for the presence of the load.

The controller U2 may be programmed or otherwise configured to employ a measure of voltage across, or current through, the output terminals 21 to maintain a desired delivery profile, for example, a constant current delivery profile. In one embodiment, the controller U2 may provide drive signals to maintain a constant, or approximately constant, current output at the output terminals 21 over at least a portion of a delivery profile. In one embodiment, the controller U2 may provide drive signals to provide an increasing current output at the output terminals 21 over at least a portion of a delivery profile. For example, the controller U2 may provide drive signals to produce an increasing current over an initial portion of a delivery profile. The increasing current may increase linearly or nonlinearly. Also for example, the controller U2 may provide drive signals to produce an increasing current over a terminal portion of a delivery profile. In one embodiment, the controller U2 may provide drive signals to provide a varying current output at the output terminals 21 over at least a portion of a delivery profile. For example, the controller U2 may provide drive signals to produce a varying current over an initial portion of a delivery profile, terminal portion of a delivery profile or some intermediate portion of a delivery profile. The current may vary periodically, for example sinusoidally, or may vary aperiodically. In the illustrated embodiment, the controller U2 sets a duty cycle of a drive signal supplied to the gate of the transistor Q1 in order to maintain a constant current output at the output terminals 21. In particular, the controller U2 may start with a low duty cycle, increasing the duty cycle until a voltage supplied at pin 1 via the current sense resistor R15 matches a reference voltage $V_{ref}$. The reference voltage $V_{ref}$ may be stored or defined internally in the controller U2, and may, for example be approximately 0.6V. The controller U2 may oscillate, or vary, the duty cycle to maintain the desired constant current operation.

In the embodiment illustrated, the indicators D5, D6 may take the form of two or more light emitting diodes (LEDs) D5, D6 electrically coupled in series. The two or more LEDs D5, D6 may be electrically coupled in parallel with a resistor R11. The LEDs D5, D6 may both produce the same color(s), when driven to emission, for example green (or green light). When lit, the LEDs D5, D6 indicate that current is flowing to the output terminals.

In the embodiment illustrated, the indicators D3, D4 may take the form of LEDs D3, D4. The LED D3 and the LED D4 are each electrically coupled between an output of the controller U2, and ground through respective resistors R6, R7. The LEDs D3, D4 may both produce the same color(s), when driven to emission. The LEDs D3, D4 may produce, for example, a color different from the color produced by the LEDs D5, D6. For example, the LEDs D3, D4 may produce red or orange light. The LEDs D3, D4 may provide a first indication during start up, or to indicate a proper start up (e.g., blinking a predetermined number of times). The LEDs D3, D4 may provide a first indication during shut down, to indicate the delivery profile is terminating or has been terminated (e.g., blinking at a predetermined rate).

In some embodiments, the controller U2 may be programmed or otherwise configured to measure at least one of a voltage, current, resistance, impedance, and the like, indicative of, for example, a delivery device type (e.g., iontophoretic delivery device type, transdermal patch type, drug delivery device, and the like), a drug type, a dosing regimen, and the like. The controller U2 may be further configured to adjust a delivery profile, for example, a current delivery profile based on the measure of at least one of a voltage, a current, a resistance, an impedance, and the like. For example, the controller U2 may be programmed or otherwise configured to query the electrically powered device 11 and based on the response of the query, adjust a delivery profile, for example, a current delivery profile.

Figure 9:
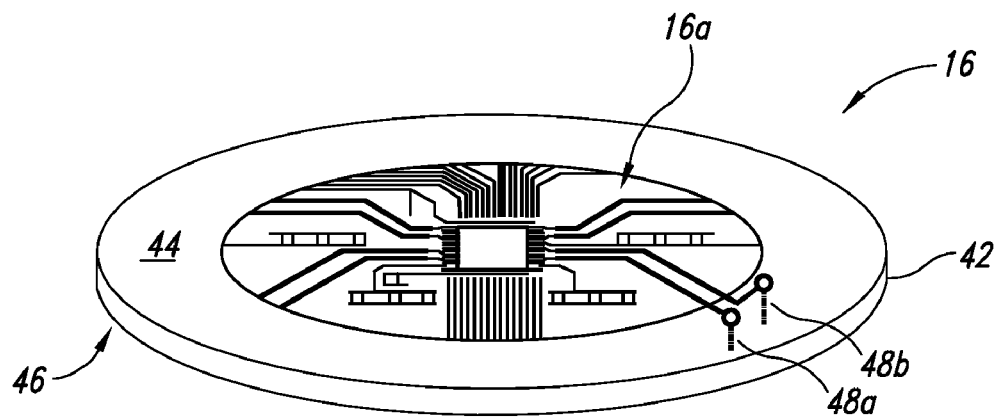
FIG. 9 is a top front view of a circuit in the form of a printed circuit according to one illustrated embodiment.
Figure 10:
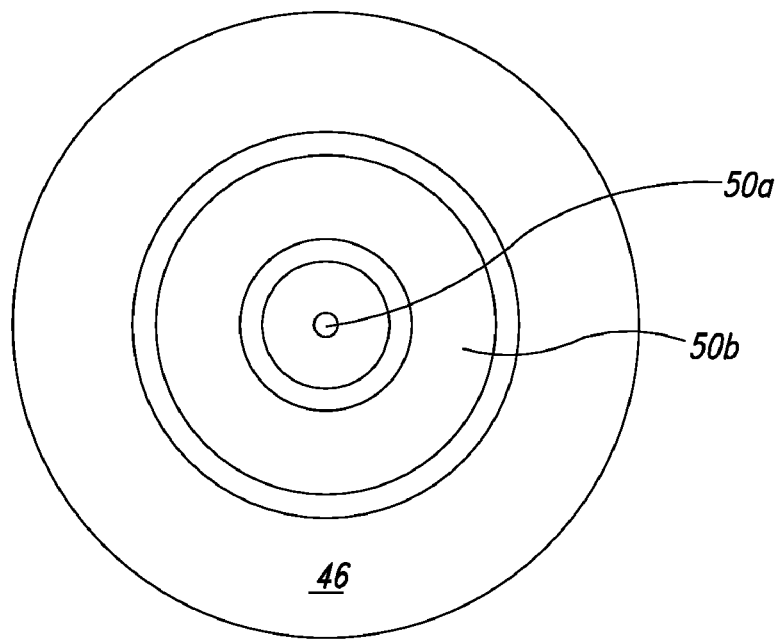
FIG. 10 is a bottom plan view of a circuit in the form of a printed circuit according to one illustrated embodiment.

Referring to FIGS. 9 and 10, the control circuit 16 may take the form of a printed circuit 16a on a substrate 42 having at least a first side 44 and a second side 46 opposite to the first side 44. The first side 44 of substrate 42 may include at least two electrical paths 48a and 48b for proving electrical communication between the power source 14 adjacent to the first side 44 and at least two conductive paths 50a and 50b on the second side 46.

In some embodiments, the at least two conductive paths 50a, 50b are configured to provide electrical communication between the portable power supply system 10 and the respective positive and negative electrical contacts of the electrically powered device 11.

Referring to FIG. 10, in some embodiments, the at least two conductive paths 50a, 50b may take the form of at least two conductive traces forming a generally concentric geometric pattern. In certain embodiments, the conductive traces may be deposited, etched, or otherwise applied to the substrate 42. The conductive trace can comprise any suitable material for making a conductive trace including conductive polymers, metallic materials, copper, gold, silver, copper coated with silver or tin, aluminum, and/or alloys or combinations thereof.

Techniques for making the circuit 16a on a substrate 42 are well known in the art and include lithographic techniques, conductive paint silk screen techniques, metal deposition, conventional pattering techniques, laser etching, and the like. For example, well-known lithographic techniques can be use to form a conductive trace layout, onto at least the first surface 44 of the substrate 42. The lithographic process for forming the conductive trace layout may include, for example, applying a resist film (e.g., spin-coating a photoresist film) onto the substrate, exposing the resist with an image of a circuit layout (e.g., the geometric pattern of one or more conductive traces), heat treating the resist, developing the resist, transferring the layout onto the substrate, and removing the remaining resist. Transferring the layout onto the substrate 42 may further include using techniques like subtractive transfer, etching, additive transfer, selective deposition, impurity doping, ion implantation, and the like.

In some embodiments, a first electrical contact 50a is electrically coupleable to a first pole of the power source 14, and a second electrical contact 50b is electrically coupleable to a second pole of the power source 14. The first and the second electrical contacts 50a, 50b are positioned to make electrical contact with a set of contacts on the electrically powered device 11 in response to the portable power supply system 10 being magnetically coupled to the electrically powered device 11 via the first magnetic coupling element 12a.

In some embodiments, the first electrical contact 50a is concentrically aligned with respect to the second electrical contact 50b. In some further embodiments, the first electrical contact 50a is at least a portion of a circular conductive trace and the second electrical contact 50b is at least a portion of a circular conductive trace.

The portable power supply system 10 is useful for providing power to electrically powered devices such as, for example, a transdermal delivery device 102.

The portable power supply system 10 may include at least one inductor electrically coupled to the power source 14 and operable to inductively transfer power from the power source 14 to the electrically powered device 11 in response to the portable power supply system 10 being magnetically coupled to the electrically powered device 11 by the first magnetic coupling element 12a. In some embodiments, the portable power supply system 10 takes the form of a portable power supply system.

FIGS. 11 and 12 show exemplary transdermal delivery systems 100 for delivering of one or more active agents to a subject. The transdermal delivery systems 100 include a transdermal delivery device 102 including active and counter electrode assemblies 112, 114, respectively, and a portable power supply system 10. The overall shape of the transdermal delivery device 102 may take a variety of geometric forms including, for example, those shown in FIGS. 11 and 12.

In some embodiments, the transdermal delivery device 102 further includes at least a first magnetic interconnect element 108 that magnetically-releasably couples the power supply system 10 to the substrate.

In some embodiments, the active electrode assembly 112 takes the form of a positive electrode assembly, and the counter electrode assembly 114 takes the form of a negative electrode assembly. Alternatively, the counter electrode assembly 114 may take the form of a negative assembly, and the active electrode assembly 114 may take the form of a positive electrode assembly. The active and counter electrode assemblies 112, 114, are electrically coupleable to the portable power supply system 10 to supply an active agent contained in the active electrode assembly 112, via iontophoresis, to a biological interface (e.g., a portion of skin or mucous membrane).

The transdermal delivery device 102 may optionally include a backing 119. In some embodiments, the backing 119 encases the transdermal delivery device 102. In some other embodiments, the backing 119 physically couples the transdermal delivery device 102 to a biological interface of a subject. In some embodiments, the transdermal delivery system 102 is configured to provide transdermal delivery of one or more therapeutic active agents to a biological interface of a subject.

Figure 13:
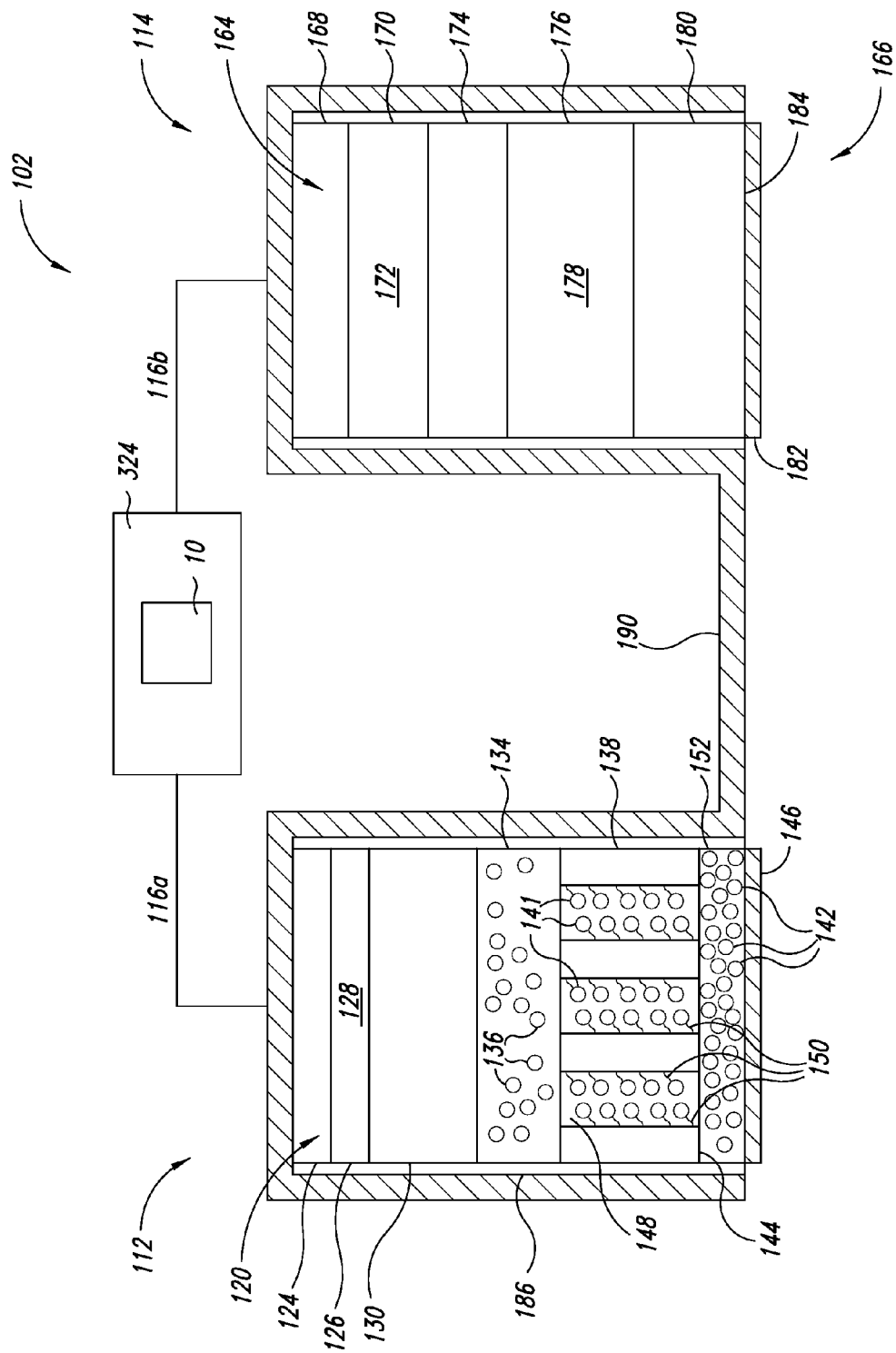
FIG. 13 is a schematic diagram of the transdermal delivery device of FIG. 11 comprising an active electrode assembly and a counter electrode assembly according to one illustrated embodiment.
Figure 14:
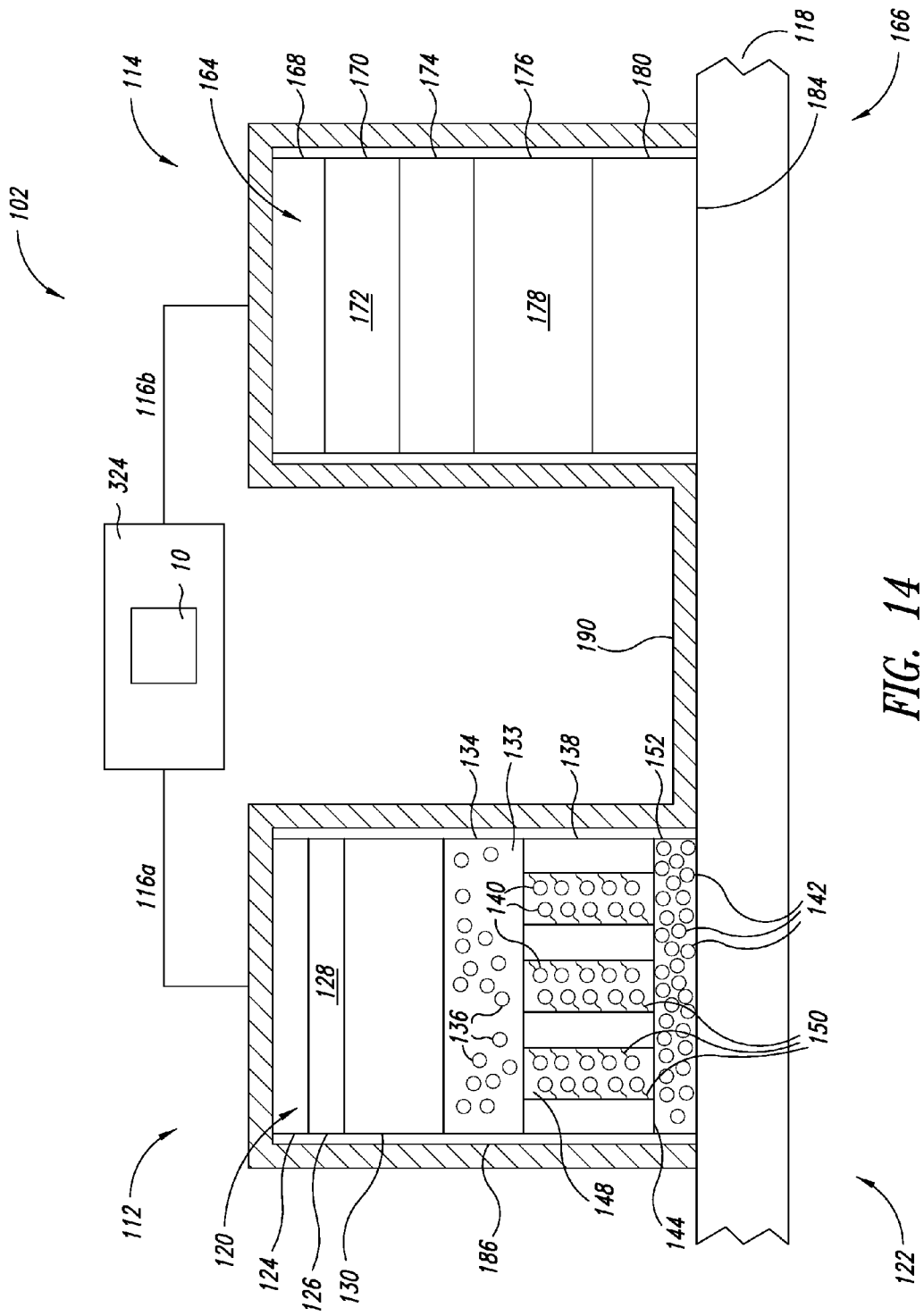
FIG. 14 is a schematic diagram of the transdermal delivery device of FIG. 13 positioned on a biological interface, with an optional outer release liner removed to expose the active agent, according to another illustrated embodiment.

As shown in FIGS. 13 and 14, the active electrode assembly 112 may further comprise, from an interior 120 to an exterior 122 of the active electrode assembly 112: an active electrode element 124, an electrolyte reservoir 126 storing an electrolyte 128, an inner ion selective membrane 130, one or more inner active agent reservoirs 134, storing one or more active agents 316, an optional outermost ion selective membrane 138 that optionally caches additional active agents 40, and an optional further active agent 142 carried by an outer surface 144 of the outermost ion selective membrane 138. Each of the above elements or structures will be discussed in detail below.

The active electrode assembly 112 may comprise an optional inner sealing liner (not shown) between two layers of the active electrode assembly 112, for example, between the inner ion selective membrane 130 and the inner active agent reservoir 134. The inner sealing liner, if present, would be removed prior to application of the iontophoretic device to the biological surface 118. The active electrode assembly 112 may further comprise an optional outer release liner 146.

In some embodiments, the one or more active agent reservoirs 134 are loadable with a vehicle and/or pharmaceutical composition for transporting, delivering, encapsulating, and/or carrying the one or more active agents 136, 140, 142. In some embodiments, the pharmaceutical composition includes a therapeutically effective one or more active agents 136, 140, 142.

The active electrode element 124 is electrically coupleable via a first pole 116a to the portable power supply system 10 and positioned in the active electrode assembly 112 to apply an electromotive force to transport the active agent 136, 140, 142 via various other components of the active electrode assembly 112. Under ordinary use conditions, the magnitude of the applied electromotive force is generally that required to deliver the one or more active agents according to a therapeutic effective dosage protocol. In some embodiments, the magnitude is selected such that it meets or exceeds the ordinary use operating electrochemical potential of the transdermal delivery device 102. The at least one active electrode element 124 is operable to provide an electromotive force for driving a pharmaceutical composition comprising one or more active agents 136, 140, 142 from the at least one active agent reservoir 134, to the biological interface 118 of the subject.

The active electrode element 124 may take a variety of forms. In one embodiment, the active electrode element 124 may advantageously take the form of a carbon-based active electrode element. Such may comprise multiple layers, for example a polymer matrix comprising carbon and a conductive sheet comprising carbon fiber or carbon fiber paper, such as that described in commonly assigned pending Japanese patent application 2004/317317, filed Oct. 29, 2004. The carbon-based electrodes are inert electrodes in that they do not themselves undergo or participate in electrochemical reactions. Thus, an inert electrode distributes current through the oxidation or reduction of a chemical species capable of accepting or donating an electron at the potential applied to the system, (e.g., generating ions by either reduction or oxidation of water). Additional examples of inert electrodes include stainless steel, gold, platinum, capacitive carbon, or graphite.

Alternatively, an active electrode of sacrificial conductive material, such as a chemical compound or amalgam, may also be used. A sacrificial electrode does not cause electrolysis of water, but would itself be oxidized or reduced. Typically, for an anode a metal/metal salt may be employed. In such case, the metal would oxidize to metal ions, which would then be precipitated as an insoluble salt. An example of such anode includes an Ag/AgCl electrode. The reverse reaction takes place at the cathode in which the metal ion is reduced and the corresponding anion is released from the surface of the electrode.

The electrolyte reservoir 126 may take a variety of forms including any structure capable of retaining electrolyte 128, and, in some embodiments, may even be the electrolyte 128 itself, for example, where the electrolyte 128 is in a gel, semi-solid or solid form. For example, the electrolyte reservoir 126 may take the form of a pouch or other receptacle, or a membrane with pores, cavities, or interstices, particularly where the electrolyte 128 is a liquid.

In one embodiment, the electrolyte 128 comprises ionic or ionizable components in an aqueous medium, which can act to conduct current towards or away from the active electrode element. Suitable electrolytes include, for example, aqueous solutions of salts. Preferably, the electrolyte 128 includes salts of physiological ions, such as sodium, potassium, chloride, and phosphate. In some embodiments, the one or more electrolyte reservoirs 124 include an electrolyte 128 comprising at least one biologically compatible anti-oxidant selected from ascorbate, fumarate, lactate, and malate, or salts thereof.

Once an electrical potential is applied, when an inert electrode element is in use, water is electrolyzed at both the active and counter electrode assemblies. In certain embodiments, such as when the active electrode assembly is an anode, water is oxidized. As a result, oxygen is removed from water while protons ($H^+$) are produced. In one embodiment, the electrolyte 128 may further comprise an anti-oxidant. In some embodiments, the anti-oxidant is selected from anti-oxidants that have a lower potential than that of, for example, water. In such embodiments, the selected anti-oxidant is consumed rather than having the hydrolysis of water occur. In some further embodiments, an oxidized form of the anti-oxidant is used at the cathode and a reduced form of the anti-oxidant is used at the anode. Examples of biologically compatible anti-oxidants include, but are not limited to, ascorbic acid (vitamin C), tocopherol (vitamin E), or sodium citrate.

As noted above, the electrolyte 128 may take the form of an aqueous solution housed within a reservoir 126, or may take the form of a dispersion in a hydrogel or hydrophilic polymer capable of retaining a substantial amount of water. For instance, a suitable electrolyte may take the form of a solution of 0.5 M disodium fumarate: 0.5 M polyacrylic acid: 0.15 M anti-oxidant.

The inner ion selective membrane 130 is generally positioned to separate the electrolyte 128 and the inner active agent reservoir 134, if such a membrane is included within the device. The inner ion selective membrane 130 may take the form of a charge selective membrane. For example, when the active agent 136, 140, 142 comprises a cationic active agent, the inner ion selective membrane 130 may take the form of an anion exchange membrane, selective to substantially pass anions and substantially block cations. The inner ion selective membrane 130 may advantageously prevent transfer of undesirable elements or compounds between the electrolyte 128 and the inner active agent reservoir 134. For example, the inner ion selective membrane 130 may prevent or inhibit the transfer of sodium ($Na^+$) ions from the electrolyte 128, thereby increasing the transfer rate and/or biological compatibility of the transdermal delivery device 102.

The inner active agent reservoir 134 is generally positioned between the inner ion selective membrane 130 and the outermost ion selective membrane 138. The inner active agent reservoir 134 may take a variety of forms including any structure capable of temporarily retaining active agent 136. For example, the inner active agent reservoir 134 may take the form of a pouch or other receptacle, or a membrane with pores, cavities, or interstices, particularly where the active agent 136 is a liquid. The inner active agent reservoir 134 further may comprise a gel matrix.

Optionally, an outermost ion selective membrane 138 is positioned generally opposed across the active electrode assembly 112 from the active electrode element 124. The outermost membrane 138 may, as in the embodiment illustrated in FIGS. 13 and 14, take the form of an ion exchange membrane having pores 148 (only one called out in FIGS. 13 and 14 for sake of clarity of illustration) of the ion selective membrane 138 including ion exchange material or groups 150 (only three called out in FIGS. 13 and 14 for sake of clarity of illustration). Under the influence of an electromotive force or current, the ion exchange material or groups 150 selectively substantially passes ions of the same polarity as active agent 136, 140, while substantially blocking ions of the opposite polarity. Thus, the outermost ion exchange membrane 138 is charge selective. Where the active agent 136, 140, 142 is a cation (e.g., lidocaine), the outermost ion selective membrane 138 may take the form of a cation exchange membrane, thus allowing the passage of the cationic active agent while blocking the back flux of the anions present in the biological interface, such as skin.

The outermost ion selective membrane 138 may optionally cache active agent 140. Without being limited by theory, the ion exchange groups or material 150 temporarily retains ions of the same polarity as the polarity of the active agent in the absence of electromotive force or current and substantially releases those ions when replaced with substitutive ions of like polarity or charge under the influence of an electromotive force or current.

Alternatively, the outermost ion selective membrane 138 may take the form of a semi-permeable or microporous membrane that is selective by size. In some embodiments, such a semi-permeable membrane may advantageously cache active agent 140, for example by employing the removably releasable outer release liner to retain the active agent 140 until the outer release liner is removed prior to use.

The outermost ion selective membrane 138 may be optionally preloaded with the additional active agent 140, such as ionized or ionizable drugs or therapeutic agents and/or polarized or polarizable drugs or therapeutic agents. Where the outermost ion selective membrane 138 is an ion exchange membrane, a substantial amount of active agent 140 may bond to ion exchange groups 150 in the pores, cavities or interstices 148 of the outermost ion selective membrane 138.

The active agent 142 that fails to bond to the ion exchange groups of material 150 may adhere to the outer surface 144 of the outermost ion selective membrane 138 as the further active agent 142. Alternatively, or additionally, the further active agent 142 may be positively deposited on and/or adhered to at least a portion of the outer surface 144 of the outermost ion selective membrane 138, for example, by spraying, flooding, coating, electrostatically depositing, vapor depositioning, and/or otherwise. In some embodiments, the further active agent 142 may sufficiently cover the outer surface 144 and/or be of sufficient thickness to form a distinct layer 152. In other embodiments, the further active agent 142 may not be sufficient in volume, thickness, or coverage as to constitute a layer in a conventional sense of such term.

The active agent 142 may be deposited in a variety of highly concentrated forms such as, for example, solid form, nearly saturated solution form, or gel form. If in solid form, a source of hydration may be provided, either integrated into the active electrode assembly 112, or applied from the exterior thereof just prior to use.

In some embodiments, the active agent 136, additional active agent 140, and/or further active agent 142 may be identical or similar compositions or elements. In other embodiments, the active agent 136, additional active agent 140, and/or further active agent 142 may be different compositions or elements from one another. Thus, a first type of active agent may be stored in the inner active agent reservoir 134, while a second type of active agent may be cached in the outermost ion selective membrane 138. In such an embodiment, either the first type or the second type of active agent may be deposited on the outer surface 144 of the outermost ion selective membrane 138 as the further active agent 142. Alternatively, a mix of the first and the second types of active agent may be deposited on the outer surface 144 of the outermost ion selective membrane 138 as the further active agent 142. As a further alternative, a third type of active agent composition or element may be deposited on the outer surface 144 of the outermost ion selective membrane 138 as the further active agent 142. In another embodiment, a first type of active agent may be stored in the inner active agent reservoir 134 as the active agent 136 and cached in the outermost ion selective membrane 138 as the additional active agent 140, while a second type of active agent may be deposited on the outer surface 144 of the outermost ion selective membrane 138 as the further active agent 142. Typically, in embodiments where one or more different active agents are employed, the active agents 136, 140, 142 will all be of common polarity to prevent the active agents 136, 140, 142 from competing with one another. Other combinations are possible.

The outer release liner may generally be positioned overlying or covering further active agent 142 carried by the outer surface 144 of the outermost ion selective membrane 138. The outer release liner may protect the further active agent 142 and/or outermost ion selective membrane 138 during storage, prior to application of an electromotive force or current. The outer release liner may be a selectively releasable liner made of waterproof material, such as release liners commonly associated with pressure sensitive adhesives.

An interface-coupling medium (not shown) may be employed between the electrode assembly and the biological interface 118. The interface-coupling medium may take, for example, the form of an adhesive and/or gel. The gel may take the form of, for example, a hydrating gel. Selection of a suitable bioadhesive gels is within the knowledge of one skilled in the relevant art.

In the embodiment illustrated in FIGS. 13 and 14, the counter electrode assembly 114 comprises, from an interior 164 to an exterior 166 of the counter electrode assembly 114: a counter electrode element 168, an electrolyte reservoir 170 storing an electrolyte 172, an inner ion selective membrane 174, an optional buffer reservoir 176 storing buffer material 178, an optional outermost ion selective membrane 180, and an optional outer release liner 182.

The counter electrode element 168 is electrically coupleable via a second pole 116b to the portable power supply system 10, the second pole 116b having an opposite polarity to the first pole 116a. In one embodiment, the counter electrode element 168 is an inert electrode. For example, the counter electrode element 168 may take the form of the carbon-based electrode element discussed above.

The electrolyte reservoir 170 may take a variety of forms including any structure capable of retaining electrolyte 172, and, in some embodiments, may even be the electrolyte 172 itself, for example, where the electrolyte 172 is in a gel, semi-solid or solid form. For example, the electrolyte reservoir 170 may take the form of a pouch or other receptacle, or a membrane with pores, cavities, or interstices, particularly where the electrolyte 172 is a liquid.

The electrolyte 172 is generally positioned between the counter electrode element 168 and the outermost ion selective membrane 180, proximate the counter electrode element 168. As described above, the electrolyte 172 may provide ions or donate charges to prevent or inhibit the formation of gas bubbles (e.g., hydrogen or oxygen, depending on the polarity of the electrode) on the counter electrode element 168 and may prevent or inhibit the formation of acids or bases or neutralize the same, which may enhance efficiency and/or reduce the potential for irritation of the biological interface 118.

The inner ion selective membrane 174 may be positioned between the electrolyte 172 and the buffer material 178. The inner ion selective membrane 174 may take the form of a charge selective membrane, such as the illustrated ion exchange membrane that substantially allows passage of ions of a first polarity or charge while substantially blocking passage of ions or charge of a second, opposite polarity. The inner ion selective membrane 174 will typically pass ions of opposite polarity or charge to those passed by the outermost ion selective membrane 180 while substantially blocking ions of like polarity or charge. Alternatively, the inner ion selective membrane 174 may take the form of a semi-permeable or microporous membrane that is selective based on size.

The inner ion selective membrane 174 may prevent transfer of undesirable elements or compounds into the buffer material 178. For example, the inner ion selective membrane 174 may prevent or inhibit the transfer of hydroxy ($OH^-$) or chloride ($Cl^-$) ions from the electrolyte 172 into the buffer material 178.

The optional buffer reservoir 176 is generally disposed between the electrolyte reservoir and the outermost ion selective membrane 180. The buffer reservoir 176 may take a variety of forms capable of temporarily retaining the buffer material 178. For example, the buffer reservoir 176 may take the form of a cavity, a porous membrane, or a gel. The buffer material 178 may supply ions for transfer through the outermost ion selective membrane 142 to the biological interface 118. Consequently, the buffer material 178 may comprise, for example, a salt (e.g., NaCl).

The outermost ion selective membrane 180 of the counter electrode assembly 114 may take a variety of forms. For example, the outermost ion selective membrane 180 may take the form of a charge selective ion exchange membrane. Typically, the outermost ion selective membrane 180 of the counter electrode assembly 114 is selective to ions with a charge or polarity opposite to that of the outermost ion selective membrane 138 of the active electrode assembly 112. The outermost ion selective membrane 180 is therefore an anion exchange membrane, which substantially passes anions and blocks cations, thereby prevents the back flux of the cations from the biological interface. Examples of suitable ion exchange membranes include the previously discussed membranes.

Alternatively, the outermost ion selective membrane 180 may take the form of a semi-permeable membrane that substantially passes and/or blocks ions based on size or molecular weight of the ion.

The outer release liner (not shown) may generally be positioned overlying or covering an outer surface 184 of the outermost ion selective membrane 180. The outer release liner may protect the outermost ion selective membrane 180 during storage, prior to application of an electromotive force or current. The outer release liner may be a selectively releasable liner made of waterproof material, such as release liners commonly associated with pressure sensitive adhesives. In some embodiments, the outer release liner may be coextensive with the outer release liner (not shown) of the active electrode assembly 112.

The transdermal delivery device 102 may further comprise an inert molding material 186 adjacent exposed sides of the various other structures forming the active and counter electrode assemblies 112, 114. The molding material 186 may advantageously provide environmental protection to the various structures of the active and counter electrode assemblies 112, 114. Enveloping the active and counter electrode assemblies 112, 114 is a housing material 190.

As best seen in FIG. 14, the active and counter electrode assemblies 112, 114 are positioned on the biological interface 118. Positioning on the biological interface may close the circuit, allowing electromotive force to be applied and/or current to flow from the portable power supply system 10, to the active electrode assembly, to the biological interface 118, and to the counter electrode assembly 114.

In use, the outermost active electrode ion selective membrane 138 may be placed directly in contact with the biological interface 118. Alternatively, an interface-coupling medium (not shown) may be employed between the outermost active electrode ion selective membrane 122 and the biological interface 118. The interface-coupling medium may take, for example, the form of an adhesive and/or gel. The gel may take, for example, the form of a hydrating gel or a hydrogel. If used, the interface-coupling medium should be permeable by the active agent 136, 140, 142.

In some embodiments, the portable power supply system 10 is selected to provide sufficient voltage, current, and/or duration to ensure delivery of the one or more active agents 136, 140, 142 from the reservoir 134 and across a biological interface (e.g., a membrane) to impart the desired physiological effect. The portable power supply system 10 may, for example, provide a voltage of 12.8 V DC, with tolerance of 0.8 V DC, and a current of 0.3 mA. The portable power supply system 10 may be selectively, electrically coupled to the active and counter electrode assemblies 112, 114 via a control circuit, for example, via carbon fiber ribbons. The transdermal delivery device 102 may include discrete and/or integrated circuit elements to control the voltage, current, and/or power delivered to the electrode assemblies 112, 114. For example, the transdermal delivery device 102 may include a diode to provide a constant current to the electrode elements 124, 168.

As suggested above, the one or more active agents 136, 140, 142 may take the form of one or more ionic, cationic, ionizeable, and/or neutral drug or other therapeutic agent. Consequently, the poles or terminals of the portable power supply system 10 and the selectivity of the outermost ion selective membranes 138, 180 and inner ion selective membranes 130, 174 are selected accordingly.

During iontophoresis, the electromotive force across the electrode assemblies, as described, leads to a migration of charged active agent molecules, as well as ions and other charged components, through the biological interface into the biological tissue. This migration may lead to an accumulation of active agents, ions, and/or other charged components within the biological tissue beyond the interface. During iontophoresis, in addition to the migration of charged molecules in response to repulsive forces, there is also an electroosmotic flow of solvent (e.g., water) through the electrodes and the biological interface into the tissue. In certain embodiments, the electroosmotic solvent flow enhances migration of both charged and uncharged molecules. Enhanced migration via electroosmotic solvent flow may occur particularly with increasing size of the molecule.

In certain embodiments, the active agent may be a higher molecular weight molecule. In certain aspects, the molecule may be a polar polyelectrolyte. In certain other aspects, the molecule may be lipophilic. In certain embodiments, such molecules may be charged, may have a low net charge, or may be uncharged under the conditions within the active electrode. In certain aspects, such active agents may migrate poorly under the iontophoretic repulsive forces, in contrast to the migration of small, more highly charged active agents under the influence of these forces. These higher molecular weight active agents may thus be carried through the biological interface into the underlying tissues primarily via electroosmotic solvent flow. In certain embodiments, the high molecular weight polyelectrolytic active agents may be proteins, polypeptides, or nucleic acids. In other embodiments, the active agent may be mixed with another agent to form a complex capable of being transported across the biological interface via one of the motive methods described above.

Figure 15:
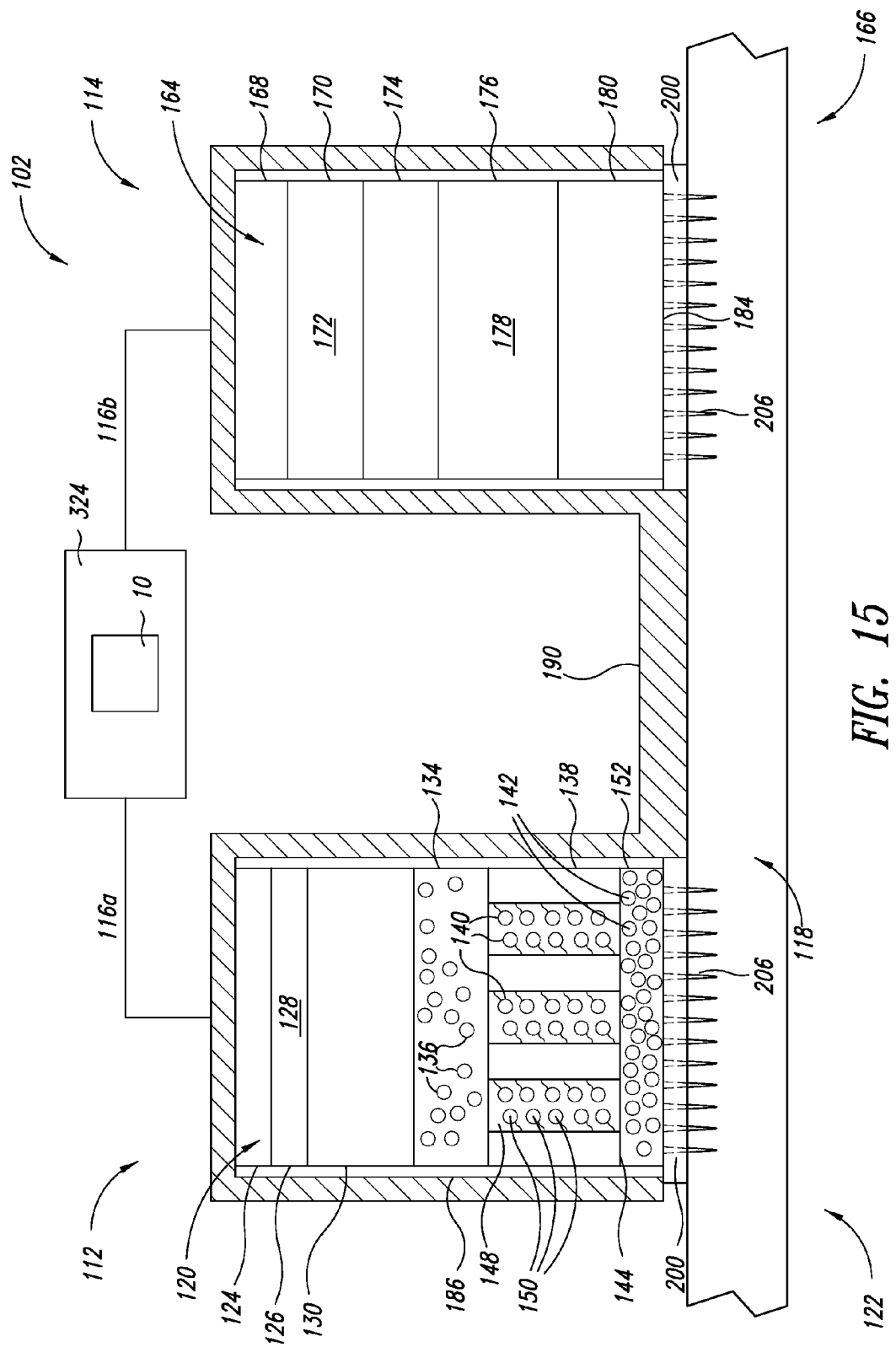
FIG. 15 is a schematic diagram of the transdermal delivery device comprising an active electrode assembly and a counter electrode assembly and a plurality of microneedles according to one illustrated embodiment.

As shown in FIG. 15, the delivery device 102 may further include a substrate 200 including a plurality of microneedles 206 in fluidic communication with the active electrode assembly 112, and positioned between the active electrode assembly 112 and the biological interface 118. The substrate 200 may be positioned between the active electrode assembly 112 and the biological interface 118. In some embodiments, the at least one active electrode element 120 is operable to provide an electromotive force to drive an active agent 136, 140, 142 from the at least one active agent reservoir 134, through the plurality of microneedles 206, and to the biological interface 118.

Figure 16:
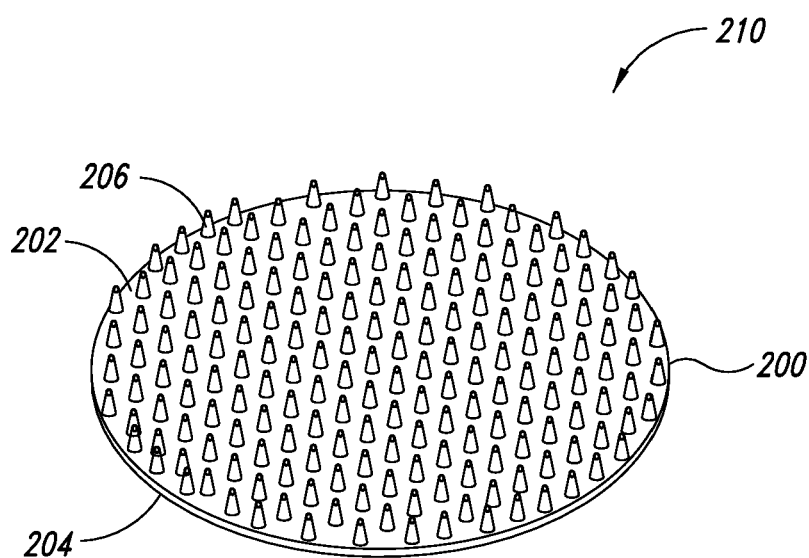
FIG. 16 is a bottom front isometric view of a plurality of microneedles in the form of an array according to one illustrated embodiment.
Figure 17:
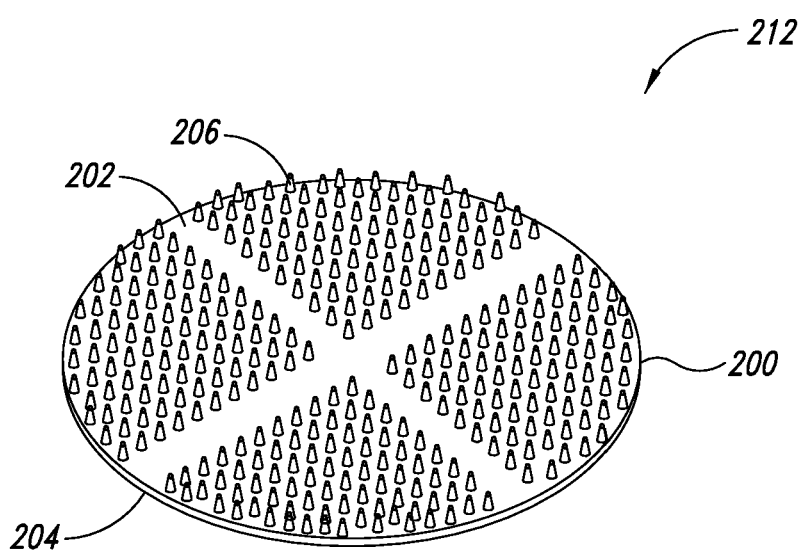
FIG. 17 is a bottom front isometric view of a plurality of microneedles in the form of one or more arrays according to another illustrated embodiment.

As shown in FIGS. 16 and 17, the substrate 200 includes a first side 202 and a second side 204 opposing the first side 202. The first side 202 of the substrate 200 includes a plurality of microneedles 206 projecting outwardly from the first side 202. The microneedles 206 may be individually provided or formed as part of one or more arrays. In some embodiments, the microneedles 206 are integrally formed from the substrate 200. The microneedles 206 may take a solid and permeable form, a solid and semi-permeable form, and/or a solid and non-permeable form. In some other embodiments, solid, non-permeable, microneedles may further comprise grooves along their outer surfaces for aiding the transdermal delivery of one or more active agents. In some other embodiments, the microneedles 206 may take the form of hollow microneedles. In some embodiments, the hollow microneedles may be filled with ion exchange material, ion selective materials, permeable materials, semi-permeable materials, solid materials, and the like.

The microneedles 206 are used, for example, to deliver a variety of pharmaceutical compositions, molecules, compounds, active agents, and the like to a living body via a biological interface, such as skin or mucous membrane. In certain embodiments, pharmaceutical compositions, molecules, compounds, active agents, and the like may be delivered into or through the biological interface. For example, in delivering pharmaceutical compositions, molecules, compounds, active agents, and the like via the skin, the length of the microneedle 206, either individually or in arrays 210, 212, and/or the depth of insertion may be used to control whether administration of pharmaceutical compositions, molecules, compounds, active agents, and the like is only into the epidermis, through the epidermis to the dermis, or subcutaneous. In certain embodiments, the microneedle 206 may be useful for delivering high-molecular weight active agents, such as those comprising proteins, peptides and/or nucleic acids, and corresponding compositions thereof. In certain embodiments, for example, wherein the fluid is an ionic solution, the microneedles 206 can provide electrical continuity between the portable power supply system 10 and the tips of the microneedles 206. In some embodiments, the microneedles 206, either individually or in arrays 210, 212, may be used to dispense, deliver, and/or sample fluids through hollow apertures, through the solid permeable or semi permeable materials, or via external grooves. The microneedles 206 may further be used to dispense, deliver, and/or sample pharmaceutical compositions, molecules, compounds, active agents, and the like by iontophoretic methods, as disclosed herein.

Accordingly, in certain embodiments, for example, a plurality of microneedles 206 in an array 210, 212 may advantageously be formed on an outermost biological interface-contacting surface of a transdermal drug delivery system 6. In some embodiments, the pharmaceutical compositions, molecules, compounds, active agents, and the like delivered or sampled by such a system 6 may comprise, for example, high-molecular weight active agents, such as proteins, peptides, and/or nucleic acids.

In some embodiments, a plurality of microneedles 206 may take the form of a microneedle array 210, 212. The microneedle array 210, 212 may be arranged in a variety of configurations and patterns including, for example, a rectangle, a square, a circle (as shown in FIG. 16), a triangle, a polygon, a regular or irregular shapes, and the like. The microneedles 206 and the microneedle arrays 210, 212 may be manufactured from a variety of materials, including ceramics, elastomers, epoxy photoresist, glass, glass polymers, glass/polymer materials, metals (e.g., chromium, cobalt, gold, molybdenum, nickel, stainless steel, titanium, tungsten steel, and the like), molded plastics, polymers, biodegradable polymers, non-biodegradable polymers, organic polymers, inorganic polymers, silicon, silicon dioxide, polysilicon, silicon rubbers, silicon-based organic polymers, superconducting materials (e.g., superconductor wafers), and the like, as well as combinations, composites, and/or alloys thereof. Techniques for fabricating the microneedles 206 are well known in the art and include, for example, electro-deposition, electro-deposition onto laser-drilled polymer molds, laser cutting and electro-polishing, laser micromachining, surface micro-machining, soft lithography, x-ray lithography, LIGA techniques (e.g., X-ray lithography, electroplating, and molding), injection molding, conventional silicon-based fabrication methods (e.g., inductively coupled plasma etching, wet etching, isotropic and anisotropic etching, isotropic silicon etching, anisotropic silicon etching, anisotropic GaAs etching, deep reactive ion etching, silicon isotropic etching, silicon bulk micromachining, and the like), complementary-symmetry/metal-oxide semiconductor (CMOS) technology, deep x-ray exposure techniques, and the like. See, for example, U.S. Pat. Nos. 6,256,533; 6,312,612; 6,334,856; 6,379,324; 6,451,240; 6,471,903; 6,503,231; 6,511,463; 6,533,949; 6,565,532; 6,603,987; 6,611,707; 6,663,820; 6,767,341; 6,790,372; 6,815,360; 6,881,203; 6,908,453; and 6,939,311. Some or all of the teachings therein may be applied to microneedle devices, their manufacture, and their use in iontophoretic applications. In some techniques, the physical characteristics of the microneedles 206 depend on, for example, the anodization conditions (e.g., current density, etching time, HF concentration, temperature, bias settings, and the like) as well as substrate properties (e.g., doping density, doping orientation, and the like).

The microneedles 206 may be sized and shaped to penetrate the outer layers of skin to increase its permeability and transdermal transport of pharmaceutical compositions, molecules, compounds, active agents, and the like. In some embodiments, the microneedles 206 are sized and shaped with an appropriate geometry and sufficient strength to insert into a biological interface 118 (e.g., the skin or mucous membrane on a subject, and the like), and thereby increase a trans-interface (e.g., transdermal) transport of pharmaceutical compositions, molecules, compounds, active agents, and the like.

Figure 18:
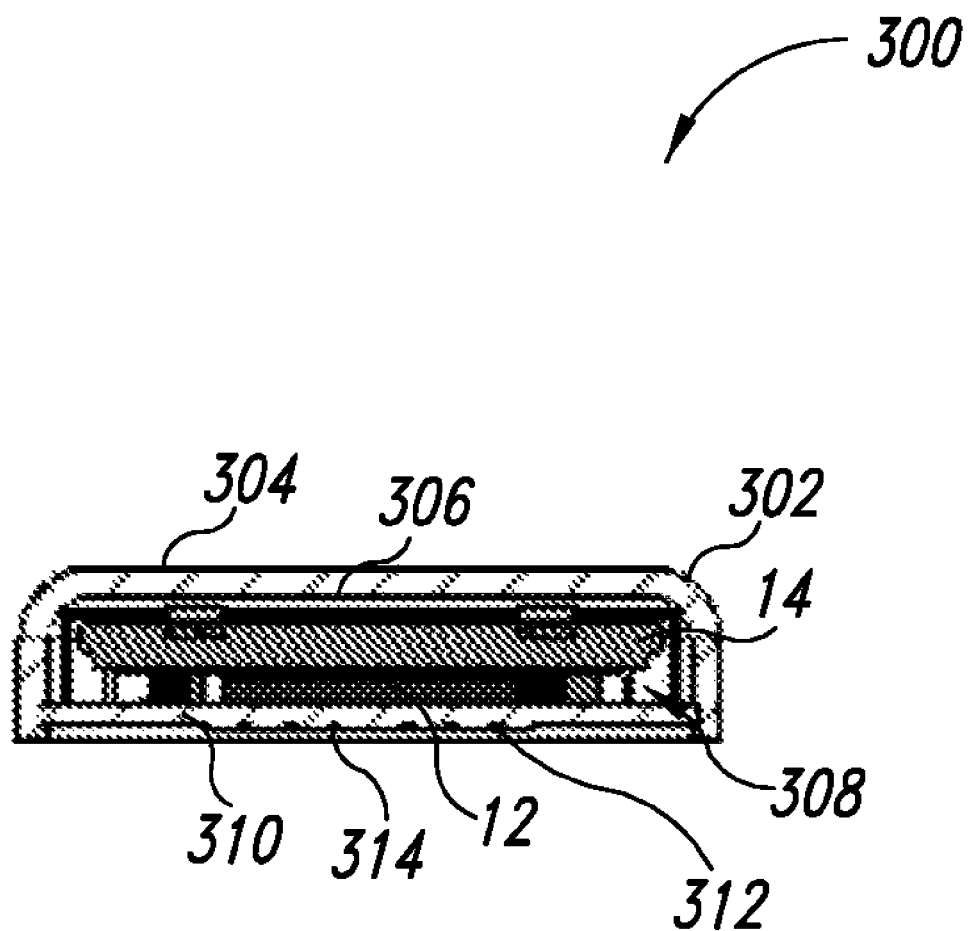
FIG. 18 is a cross-sectional view of an encapsulated battery assembly for powering a transdermal delivery device according to one illustrated embodiment.

FIG. 18 shows an exemplary encapsulated battery assembly 300 for powering a transdermal delivery device 102. The encapsulated battery assembly includes a housing 302 having an exterior surface 304 and an interior surface 306, the interior surface 306 defining an isolated space 308. The encapsulated battery assembly 300 further includes the power source 14 received in the isolated space 308 of the housing 302, and a control circuit 310 received in the isolated space 308 of the housing 302. The encapsulated battery assembly 300 may further include coupler 12 in the form of an electromagnetic coupler to magnetically couple the encapsulated battery assembly 300 to the transdermal drug delivery device 102. In some embodiments, the electromagnetic coupler is operable to auto-decouple from the transdermal drug delivery device 102 when a power level of the power source 14 is less than a threshold level.

In some embodiments, the encapsulated battery assembly 300 includes means for transferring power to at least one electrode 124, 168 of the transdermal delivery device 102 from the power source 14 in response to the encapsulated battery assembly 300 being releasably coupled to the transdermal delivery device 102.

In some embodiments, the means for transferring power includes at least two electrical paths 312 and 314 on the exterior surface 304 of the housing 302 to provide electrical communication between the power source 14 and the at least one electrode 124, 168 of the transdermal delivery device 102 when the encapsulated battery assembly 300 is releasably coupled to the transdermal delivery device 102.

Figure 19:
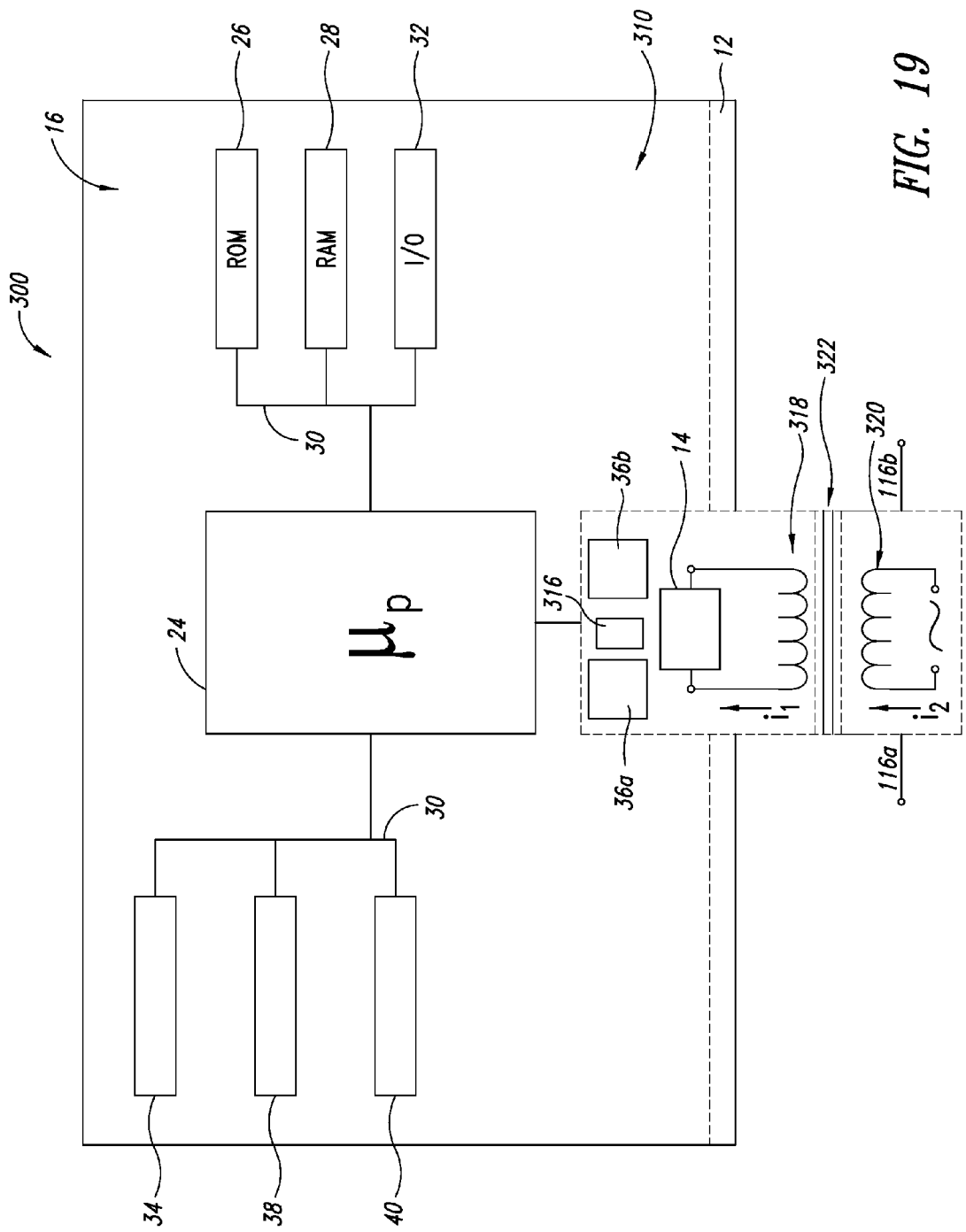
FIG. 19 is a functional block diagram showing an encapsulated battery assembly for inductively powering a transdermal delivery device according to one illustrated embodiment.

As shown in FIG. 19, in some embodiments, the encapsulated battery assembly 300 may be operable to transfer energy to the transdermal delivery device 102 via inductive coupling. The transfer of energy results in part from the mutual inductance between the components. For example, a change in current flow ($i_1$) through one component may induce a current flow ($i_2$) in the other component. In some embodiments, the encapsulated battery assembly 300 is operable to transfer energy, via inductive coupling, from a primary inductor 318 to a secondary inductor 320 through a shared magnetic field 322.

In some embodiments, the means for transferring power may include an inverter 316 to provide an alternating current and at least one primary winding 318 coupled to receive the alternating current and positioned to induce a current flow in a secondary winding 320 of the transdermal delivery device 102 when the encapsulated battery assembly 300 is releasably coupled to the transdermal delivery device 102. The means for transferring power may also include a rectifier electrically coupled to the secondary winding 320 to produce a direct current across an electrode 124, 168 of the transdermal delivery device 102.

The windings 318, 320 may include one or more complete turns of a conductive material in a coil, and may comprise one or more layers. Examples of suitable conductive materials include conductive polymers, metallic materials, copper, gold, silver, copper coated with silver or tin, aluminum, and/or alloys or combinations thereof. In some embodiments, the windings 318, 320 may comprise, for example, solid wires, including, for example, flat wires, strands, twisted strands, sheets, and the like. Examples of primary windings 318 include a coil, a winding, a primary coil, a primary winding, an inductive coil, a primary inductor, and the like. Examples of secondary windings 320 include a coil, a winding, a secondary coil, a secondary winding, an inductive coil, a secondary inductor, and the like. The secondary windings 320 may include one or more complete turns of a conductive material in a coil, and may comprise one or more layers. The encapsulated battery assembly 300 may further include the power source 14 (e.g., a rechargeable power source) coupled to the active and counter electrode assemblies 112, 114, and electrically coupled in parallel with the secondary windings 320 to receive a charge thereby. The encapsulated battery assembly 300 in the form of an inductive power supply may be operable to provide at least one of an alternating current or a pulsed direct current to the primary winding 310.

The encapsulated battery assembly 300 may further include a magnetic coupler 12 in the form of a permanent magnet to releasably-magnetically couple the encapsulated battery assembly 300 to the transdermal delivery device 102. In some embodiments, the magnetic coupler 12 takes the form of a ferrous metal element to magnetically couple the encapsulated battery assembly 300 to a magnet carried by the transdermal delivery device 102.

The circuit 310 is operable to control a voltage and a current of the power delivered to the at least one electrode assembly 112, 114 of the transdermal delivery device 102. In some embodiments, the circuit 310 is operable to vary a current provided to the transdermal delivery device 102 according to a delivery profile associated with an active agent. Examples of the circuit 310 include programmable circuits, inductively programmable circuits, integrated circuits, discrete circuits, and the like. In some embodiments, the circuit 310 takes the form of a programmable circuit. In some embodiments, the circuit 310 takes the form of an inductively programmable circuit. In some further embodiments, the circuit 310 takes the form of an integrated circuit.

Figure 20:
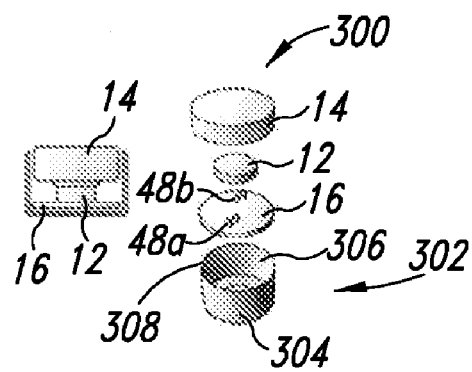
FIG. 20 is an unexploded and an exploded view of an encapsulated battery assembly for powering a transdermal delivery device according to another illustrated embodiment.
Figure 21:
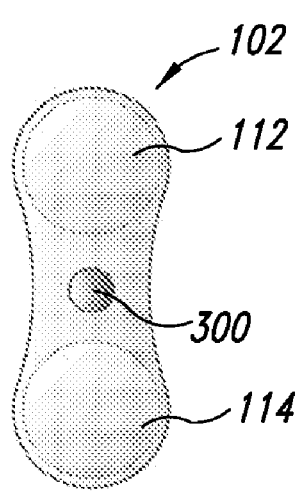
FIG. 21 is a top plan view of a transdermal delivery device according to one illustrated embodiment.
Figure 22:
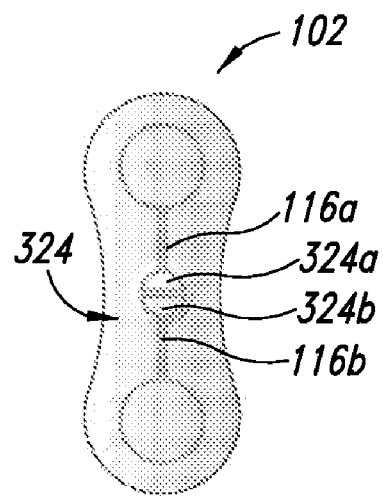
FIG. 22 is a top plan view of a transdermal delivery device according to another illustrated embodiment.

FIG. 20 shows another exemplary encapsulated battery assembly 300 for powering a transdermal delivery device 102. The encapsulated battery assembly includes a housing 302 having an exterior surface 304 and an interior surface 306. The interior surface 306 defines an isolated space 308. The encapsulated battery assembly 300 further includes power source 14 received in the isolated space 308 of the housing 302, and a control circuit 310 received in the isolated space 308 of the housing 302. The encapsulated battery assembly 300 may further include a magnetic coupler 12 to releasably-magnetically couple the encapsulated battery assembly 300 to the transdermal delivery device 102. In some embodiments, the magnetic coupler 12 takes the form of a permanent magnet to releasably-magnetically couple the encapsulated battery assembly 300 to the transdermal delivery device 102. As shown in FIG. 22, in some embodiments, the transdermal delivery device 102 includes a second magnetic coupler 324 to magnetically couple the encapsulated battery assembly 300. In some embodiments, the second magnetic coupler 324 takes the form of a ferrous metal element 324a, 324b to magnetically couple the encapsulated battery assembly 300 to a magnet carried by the transdermal delivery device 102.

Figures 23, 24:
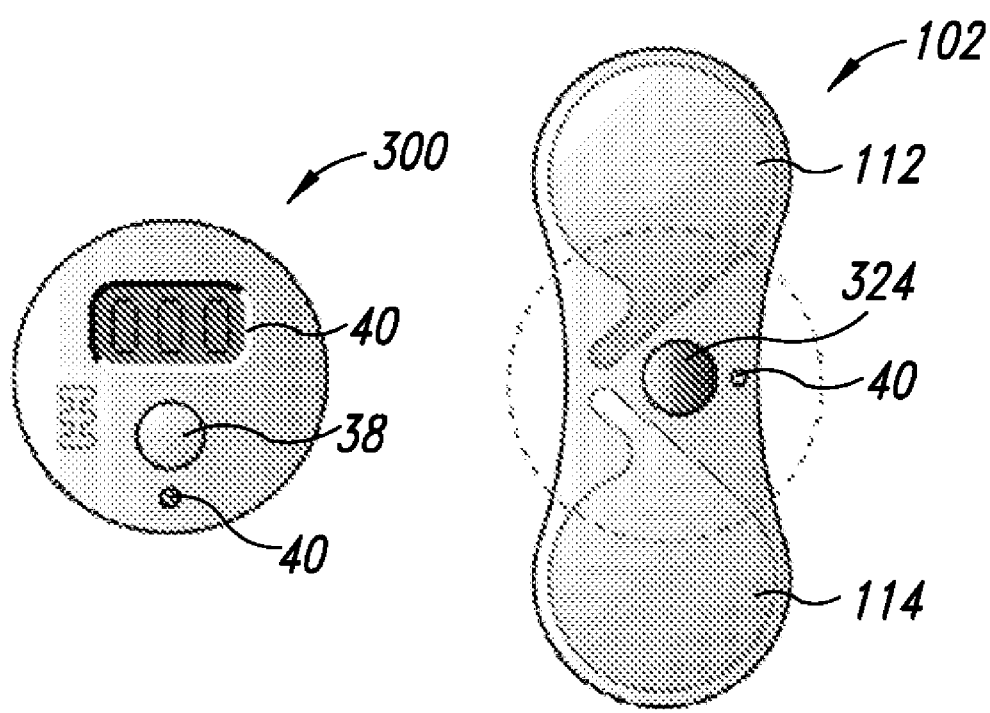
FIG. 23 is a top plan view of an encapsulated battery assembly for powering a transdermal delivery device according to another illustrated embodiment.
FIG. 24 is a top plan view of a transdermal delivery device according to one illustrated embodiment.

FIG. 23 shows another exemplary encapsulated battery assembly 300 to power and control the transdermal delivery device 102. The encapsulated battery assembly 300 may include one or more indicators 40 to, for example, alert a user that the portable power supply system 10 is operating properly. Examples of the one or more indicators 40 include visual feedback elements (e.g., green LEDs, red LEDs, a display, and the like), and audio feedback elements (e.g., an alarm, and the like). The power encapsulated battery assembly 300 may further include a start and/or stop switch 38 for selectively controlling the flow of current to the control circuit 310. The switch 38 may take the form of a dome switch, a membrane switch, a tactile switch, a single-use dome switch, a single-use membrane switch, a single-use tactile switch, and the like. As shown in FIG. 24, the transdermal delivery device 102 may also include a magnetic coupler 324 to releasably-magnetically couple the encapsulated battery assembly 300 to the transdermal delivery device 102. In some embodiments, the magnetic coupler 324 takes the form of a ferrous metal element. In some other embodiments, the magnetic coupler 324 takes the form of a permanent magnet. The transdermal delivery device 102 may also include one or more indicators 40.

Figures 25, 26:
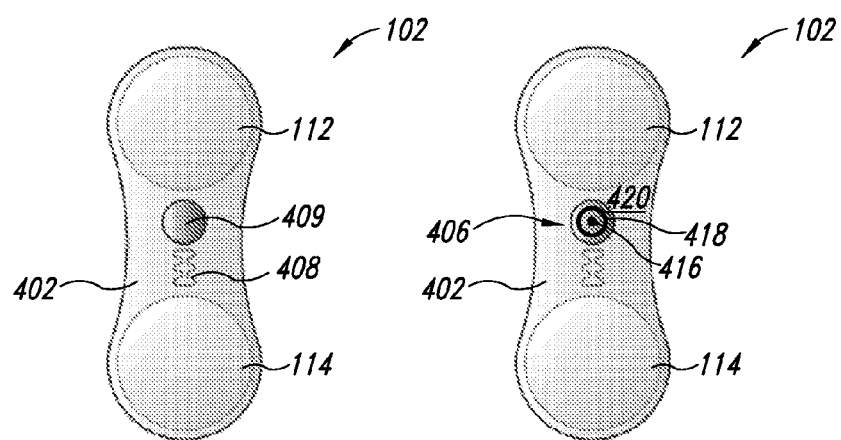
FIG. 25 is a top plan view of a transdermal delivery device according to one illustrated embodiment.
FIG. 26 is a top plan view of a transdermal delivery device according to one illustrated embodiment.

FIGS. 25 and 26 show multiple examples of a transdermal delivery device 102. The transdermal delivery device 102 may include a substrate 402. The transdermal delivery device 102 may further include an active electrode assembly 112, and/or a counter electrode assembly 114. The counter electrode assembly 114 includes at least one counter electrode element 168. The active electrode assembly 112 includes at least one active agent reservoir 134 and at least one active electrode element 124 operable to provide an electromotive force to drive an active agent 136, 140, 142 from the at least one active agent reservoir 134 to a biological interface 118 of subject. The active and counter electrode assemblies 112, 114 are each carried by the substrate 402. In some embodiments, the transdermal delivery device 102 may further include one or more active agents 136, 140, 142 loaded in the at least one active agent reservoir 134.

The transdermal delivery device 102 further includes a power supply 404, at least a first magnetic interconnect element 406, and a control circuit 408.

The at least first magnetic interconnect element 406 magnetically-releasably couples the power supply 404 to the substrate 402. In some embodiments, the first magnetic interconnect element 406 releasably attaches the power supply 404 to a negative electrical contact 418 and a positive electrical contact 416 carried by the substrate 402 in a correct electrical polarity. In some embodiments, first magnetic interconnect element 406 is electrically coupled to one pole of the power supply 404 and forms an electrical contact.

In some embodiments, the power supply 404 is operable to provide a current ranging from about 10 mA·min to about 80 mA·min for a period ranging from about 1 min to about 24 hrs.

The first magnetic interconnect element 406 may include at least a first conductive trace 416 and a second conductive trace 418 in the form of at least a first geometric shape 416a and a second geometric shape 418a. The negative and the positive electrical contacts 418, 416 on the transdermal delivery device 102 may further include at least a third conductive trace 416b and a fourth conductive trace 418b, respectively, in the form of at least a third geometric shape 416b and a fourth geometric shape 418b.

The control circuit 408 is electrically coupleable to provide a voltage across the counter and the active electrode elements 168, 124, of the transdermal delivery device 102, from the power source 14 carried by the power supply 404 during at least a portion of a period when the power supply 404 is magnetically-releasably coupled to the substrate 402. In some embodiments, the control circuit 408 takes the form of a programmable control circuit operable to provide at least a first active agent delivery profile. In some embodiments, the control circuit 408 takes the form of a programmable control circuit operable to provide at least one active agent delivery profile associated with a control delivery or a sustain delivery of the active agent. Further examples of programmable delivery profiles include programmable current profiles tailored to the delivery of specific active agents, ramp-up and auto-shut off functionality, bolus dose followed by a dose delivery regimen, digital pulse-width modulation of the current source tailored to drug delivery requirements (e.g., pseudo constant current using pulse width modulation), and the like.

The control circuit 408 may include a switch 409 selectively operable to control a supply of current to at least one of the counter and the active electrode elements 168, 124, from the power source 14, when the power supply 404 is magnetically-releasably attached to the substrate 402. In some embodiments, the control circuit 408 provides the voltage across the counter and the active electrode elements 168, 124 in response to the power supply 404 being magnetically-releasably coupled to the substrate 402.

Figures 27, 28:
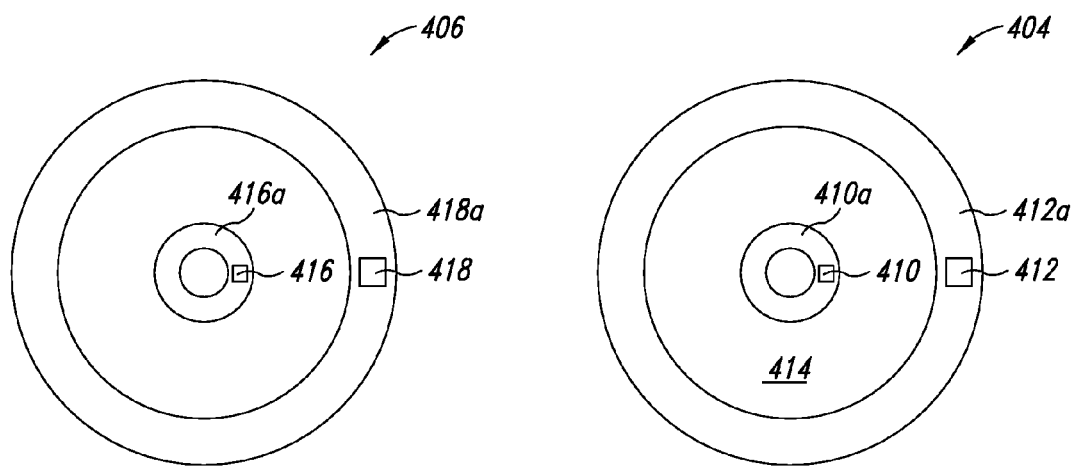
FIG. 27 is a top plan view of a magnetic interconnect element for a transdermal delivery device according to one illustrated embodiment.
FIG. 28 is a bottom plan view of a power supply for powering a transdermal delivery device according to one illustrated embodiment.

As shown in FIGS. 27 and 28, the power supply 404 may include a positive electrical contact 410 carried on an exterior 414 of the power supply 404, a negative electrical contact 412 carried on the exterior 414 of the power supply 404, a positive electrical contact 416 carried on an exterior 420 of the substrate 402, and a negative electrical contact 418 carried on an exterior 420 of the substrate 402. In some embodiments, the positive and the negative electrical contacts 410, 412 of the power supply 404 are positioned with respect to one another such that the positive electrical contact 410 of the power supply cannot contact the negative electrical contact 418 of the substrate 406 if the negative electrical contact 412 of the power supply is in contact with the positive electrical contact 416 of the substrate 402 and such that the negative electrical contact 412 of the power supply 404 cannot contact the positive electrical contact 416 of the substrate 402 if the positive electrical contact 410 of the power supply 404 is in contact with the negative electrical contact 418 of the substrate 406.

In some embodiments, the transdermal delivery device 102 may further include a first electrical contact 410a of the power supply 404 and a second electrical contact 412a of the power supply 404 such that the second electrical contact 412a is concentrically positioned with respect to the first electrical contact 410. As shown in FIG. 28 in some embodiments, the first electrical contact 410a is annular.

Figure 29:
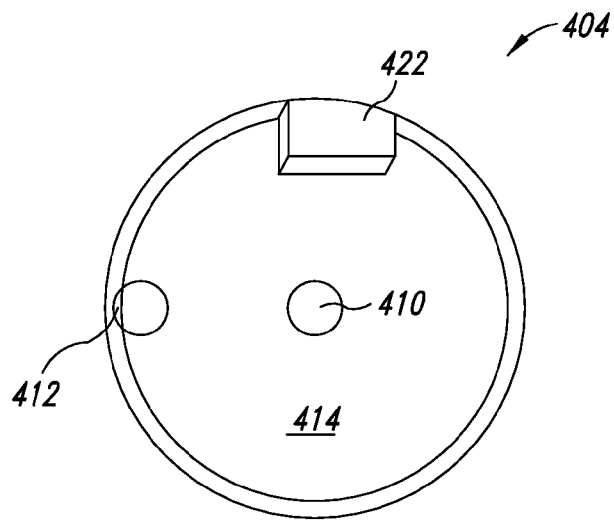
FIG. 29 is a bottom plan view of a power supply for powering a transdermal delivery device according to one illustrated embodiment.
Figure 30:
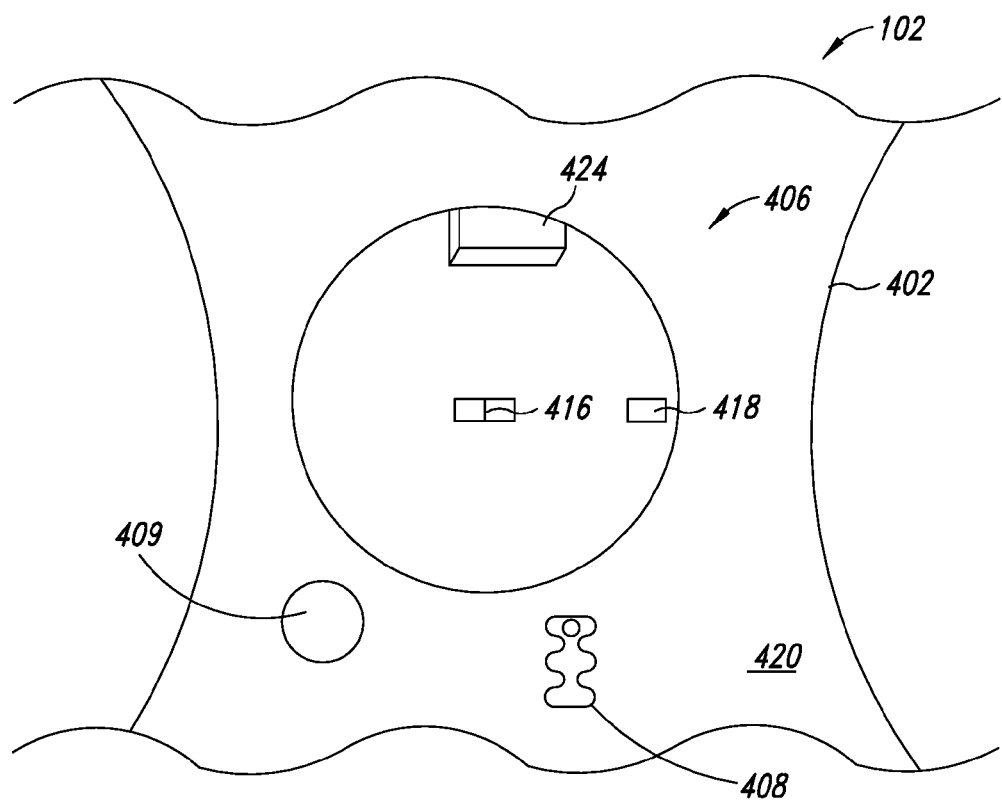
FIG. 30 is a top plan view of a portion of a transdermal delivery device including a first magnetic interconnect element according to one illustrated embodiment.

As shown in FIGS. 29 and 30, in some embodiments, the transdermal delivery device 102 may further include an alignment structure 422 carried by the power supply 404, and an alignment structure 424 carried by the substrate 402. The alignment structure 422 carried by the power supply 404 physically engages the alignment structure 424 carried by the substrate 402 such that the positive electrical contact 410 of the power supply 404 cannot contact the negative electrical contact 418 of the substrate 402 if the negative electrical contact 412 of the power supply 404 is in contact with the positive electrical contact 416 of the substrate 402 and such that the negative electrical contact 412 of the power supply 404 cannot contact the positive electrical contact 416 of the substrate 402 if the positive electrical contact 410 of the power supply 404 is in contact with the negative electrical contact 418 of the substrate 402.

Figure 31:
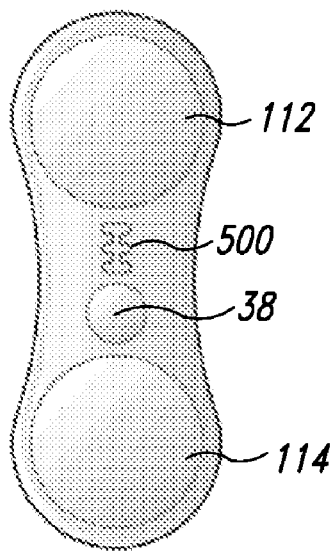
FIG. 31 is a top plan view of an iontophoretic drug delivery system for providing transdermal delivery of one or more active agents according to one illustrated embodiment.
Figure 32:
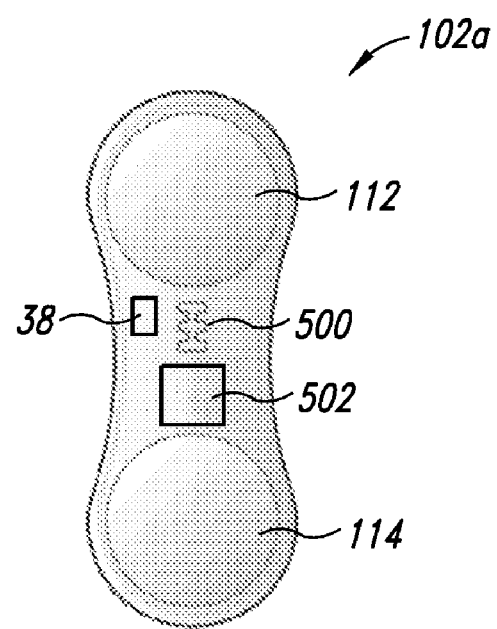
FIG. 32 is a top plan view of an iontophoretic drug delivery system for providing transdermal delivery of one or more active agents according to one illustrated embodiment.

FIGS. 31 and 32 show an exemplary iontophoretic drug delivery system 102 for providing transdermal delivery of one or more active agents to a biological interface of a subject. The iontophoretic drug delivery system 102 includes a counter electrode assembly 114, and an active electrode assembly 112. The active electrode assembly 112 may include at least one active agent reservoir 134, and may be operable to provide an electromotive force to drive at least some of the at least one active agent 136, 140, 142 from the at least one active reservoir 134 to the biological interface 118. The iontophoretic drug delivery system 102 may further include a flexible circuit 500 electrically coupled to the counter and active electrode assemblies 114, 112. The flexible circuit 500 is operable to control an electromotive force supplied to the active electrode assembly 112. Examples of flexible circuits include single-sided flexible circuits, double-sided flexible circuits, multi-layered flexible circuits, adhesiveless flexible circuits, lightweight flexible circuits, rigid-flex circuits, and the like.

In some embodiments, the flexible circuit 500 comprises a printed electronic circuit. In some embodiments, the flexible circuit 500 comprises a thin-film integrated circuit. In some embodiments, the flexible circuit 500 is less than about 7000 µm thick and a portion of the flexible circuit 500 is flexible about at least one bend axis. In some embodiments, the flexible circuit includes a conductive drug reservoir. In some embodiments, the flexible circuit comprises one or more portions fabricated from conductive fabric.

The iontophoretic drug delivery system 102 may also include a printed power source 502 electrically coupled to the flexible circuit 500. The printed power source 502 is operable to supply an electromotive force to the active electrode assembly 112. Examples of the printed power source 502 include thin-flexible power sources, thin-flexible printed batteries, POWER PAPER™, printed batteries, energy cell laminates, and the like. In some embodiments, the printed power source 502 comprises at least one printed battery. In some embodiments, the printed power source 502 comprises at least one energy cell laminate.

Figures 33, 34:
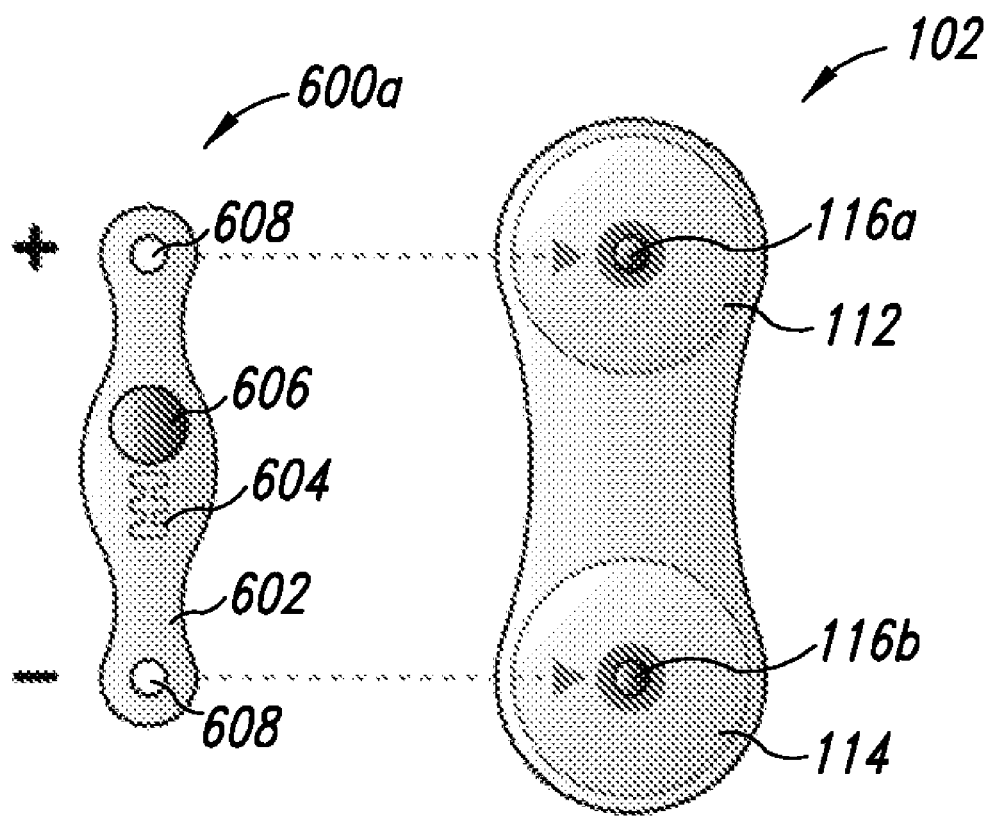
FIG. 33 is a top plan view of a detachable controller for a transdermal drug delivery device according to another illustrated embodiment.
FIG. 34 is a top plan view of a transdermal drug delivery device according to one illustrated embodiment.

FIG. 33 shows an exemplary detachable controller 600a for a transdermal drug delivery device 102. In some embodiments, the detachable controller 600a includes a substrate 602. The substrate 602 may include a control circuit 604, a power source 606 electrically coupleable to the control circuit 604, and one or more coupling elements 608 for physically coupling the detachable controller 600a to the transdermal drug delivery device 102. In some embodiments, the substrate 602 is a bendable substrate.

The power source 606 may comprise at least one of a printed battery, an energy cell laminate, a thin-film battery, a printed paper, and the like. In some embodiments, the power source 606 comprises an ultra-thin flexible power source. In some embodiments, the power source 606 is less than 1000 µm thick and flexible about at least one bend axis.

Figures 35, 36:
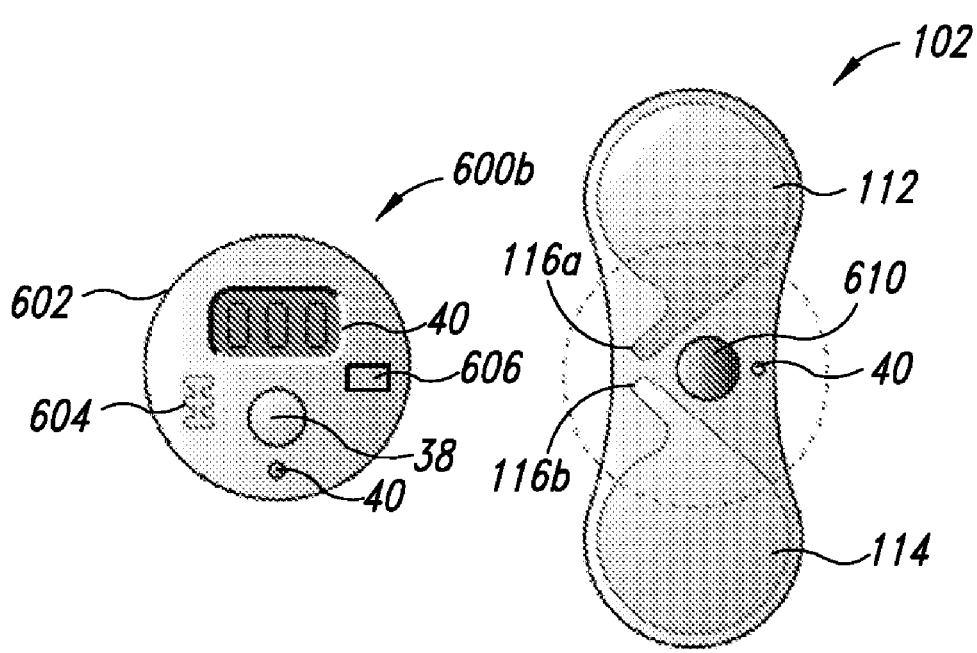
FIG. 35 is a top plan view of a detachable controller for a transdermal drug delivery device according to another illustrated embodiment.
FIG. 36 is a top plan view of a transdermal drug delivery device according to one illustrated embodiment.

FIG. 35 shows another exemplary detachable controller 600b for a transdermal drug delivery device 102 (see FIG. 36). In some embodiments, the detachable controller 600b includes a substrate 602. The substrate 602 may include a control circuit 604, a power source 606 electrically coupleable to the control circuit 604, and one or more coupling elements 608 for physically coupling the detachable controller 600b to the transdermal drug delivery device 102. In some embodiments, the substrate 602 is a bendable substrate. The detachable controller 600b may further include an electromagnetic coupler 610 to magnetically couple the detachable controller 600b to the transdermal drug delivery device 102.

The electromagnetic coupler 610 is configured to magnetically couple the detachable controller 600b to a negative electrical contact 612 and a positive electrical contact 614 on the transdermal delivery device 102 in correct electrical polarity. In some embodiments, the transdermal delivery device 102 includes visual confirmation elements capable of alerting a user that the transdermal delivery device 102 is functioning properly. For example, the transdermal delivery device 102 may further include an interconnect interface 611 configured to provide visual and/or audio confirmation that the transdermal delivery device 102 is functioning properly. For example, the interface 611 may include a waveguide configured to radially shine light through to indicate that the controller 600b is properly releasably attached to the transdermal delivery device 102.

In some embodiments, the detachable controller 600b comprises at least a first conductive trace 616 and a second conductive trace 618 electrically coupled to corresponding negative and positive current elements 616a, 618a of the detachable controller 600b. In some embodiments, the at least first and second conductive traces 616, 618 correspond to respective at least third and fourth conductive traces 620, 622 located on the transdermal delivery device 102, such that when the detachable controller 600b is magnetically coupled to the transdermal delivery device 102, the first and the second conductive traces 616, 618 are in electrical communication with the third and the fourth conductive traces 620, 622 in a correct polarity. The detachable controller 600b may further include an auto-close circuit 634 configured to automatically complete the control circuit 604 after physically coupling the detachable controller 600b to the transdermal drug delivery device 102.

In some embodiments, the transdermal drug delivery device 102 may be wirelessly coupled to a control system 600b that communicates with the transdermal drug delivery device 102 via wireless communication. Examples of wireless communication include for example, optical connections, ultraviolet connections, infrared, BLUETOOTH®, Internet connections, network connections, and the like. An internal power source may render the control system 600b cordless and allow for maximum portability of the transdermal drug delivery device 102. Alternatively, the control system 600b may remain stationary in a fixed location such that the control system 600b can be powered by coupling it to an electrical socket. In some embodiments, the control system 600b takes the form of an external remote control system.

In some embodiments, the control system 600b is configured to send and/or receive an encrypted data stream to and from the transdermal drug delivery device 102. In some embodiments, the control system 600b is configured to activate the power supply to the transdermal drug delivery device 102. For example, the control system 600b may take the form of a remote control system that allows an authorized user (e.g., a doctor) to send an encrypted data stream to activate the power supply and/or activate a treatment regimen.

In some embodiments, the control system 600b may be configured to detect the transdermal drug delivery device 102, activate the transdermal drug delivery device 102, authenticate use authorization, authenticate prescribed dosing, administer dose according to a prescribed regimen, and the like. In some embodiments, the control system 600b may be configured to detect the transdermal drug delivery device 102, and determine the associated drug type, dosing regimen, type of patch, and the like.

Figure 37:
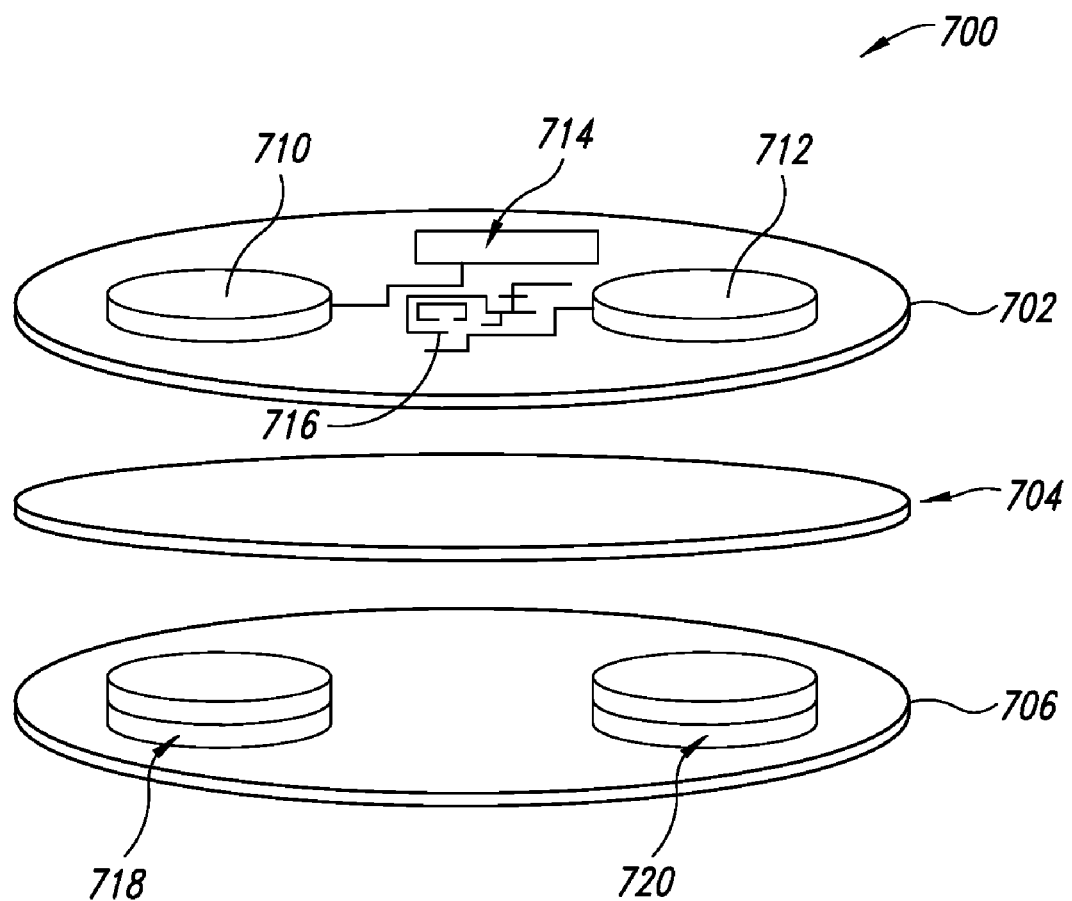
FIG. 37 is an exploded view of a transdermal drug delivery device according to one illustrated embodiment.

FIG. 37 shows an exemplary iontophoretic drug delivery system 700 for providing transdermal delivery of one or more active agents to a biological interface of a subject. The iontophoretic drug delivery system 702 includes a power supply layer 702, an interconnect layer 704, and a patch layer 706.

The power supply layer 702 may include a printed circuit 716, as well as active and counter electrodes 710, 712. In some embodiments, the printed circuit 716 may be configured to query tag data (e.g., a Radio Frequency Identification (RFID) tag) including for example stored data codes, user data, patient data, drug delivery device data, and the like. The power supply layer 702 may further include a power source 714. The power source 714 may take the form of at least one printed battery, energy cell laminate, thin-film battery, power paper, and the like, or combinations thereof.

The interconnect layer 704, may comprise any suitable materials and/or constructing for laminating, layering, physically coupling, electrically coupling, attaching, and like, the power supply layer 702 to the patch layer 706. In some embodiments, the interconnect layer 704, may comprise any suitable materials for separating and/or isolating the power supply layer 702 from the patch layer 706.

In some embodiments, at least a portion of the interconnect layer 704 may releasably attach and/or releasably coupled the power supply layer 702 to the patch layer 706 using, for example, an interconnect system. In some embodiments, the interconnect system may include a ferrous paint element releasably attachable and/or releasably coupled to a magnetic substrate. In some embodiments, the interconnect system may include a ferrous substrate releasably attachable and/or releasably coupled to a magnetic substrate. In some embodiments, the interconnect system may include a ferrous substrate releasably attachable and/or releasably coupled to a magnetic paint element. In some embodiments, the interconnect system may include a ferrous paint element releasably attachable and/or releasably coupled to a magnetic paint element. In some embodiments, the interconnect system may include a hook and loop fastener interconnect system. In some embodiments, the interconnect system may include a multi-part EKG/ECG type interconnect using, for example, concentrically patterned fasteners. In yet some other embodiments, the interconnect system may include a slot type interconnect system.

In some embodiments, at least a portion of the interconnect layer 704, may electrically, inductively, and/or capacitively couple the power supply layer 702 to the patch layer 706 using one or more power coupling structures.

In some embodiments, the one or more power coupling structures include one or more contacts, leads, terminals, inductors, or plates, which are or may be positioned with respect to one another to effectively transfer power between a power supply carried in the power supply layer 702 and the patch layer 706.

The patch layer 706 may include active and counter electrode assemblies 718, 720 that are associated with the active and counter electrode elements 710, 712 respectively. Similar to the previously described active electrode assembly 112 the active electrode assembly 718 may include one or more electrolyte reservoirs 126 storing an electrolyte 128, inner ion selective membranes 130, inner active agent reservoirs 134, storing one or more active agents 316, optional outermost ion selective membranes 138 that optionally caches additional active agents 40, optional further active agent 142 carried by an outer surface 144 of the outermost ion selective membrane 138, and optional outer release liners 146.

Similar to the previously described counter electrode assembly 114 the counter electrode assembly 718 may include one or more electrolyte reservoirs 170 storing an electrolyte 172, inner ion selective membranes 174, optional buffer reservoirs 176 storing buffer material 178, optional outermost ion selective membranes 180, and optional outer release liners 182. The iontophoretic drug delivery system 700 may optionally include a backing 119.

In some embodiments, the patch layer 706 may include an electrode layering that includes two-electrode capacitive coupling. The electrode layering may include an electrode layer configured to carry a current and etched on at least two portions of the patch layer 706, for example, on a top surface and a bottom surface, and to could create a capacitor. For example, in some embodiments, the patch layer 706 may include two or more of such capacitors configured to communicate information (e.g., type of patch, drug type, and the like) associated with the iontophoretic drug delivery system 700. In some embodiments, a control circuit carried by the power supply layer 702 may be operable to charge and discharge the one or more capacitors, and use the discharge of the capacitors to communicate information associated with the iontophoretic drug delivery system 700. In some further embodiments, a control circuit carried by the power supply layer 702 may be operable to energize or discharge a capacitor and retrieve information associated with the iontophoretic drug delivery system 700.

In some embodiments, a backing encases the iontophoretic drug delivery system 700. In some other embodiments, the backing physically couples the iontophoretic drug delivery system 700 to a biological interface of a subject. In some embodiments, the iontophoretic drug delivery system 700 is configured to provide transdermal delivery of one or more therapeutic active agents to a biological interface of a subject.

In some embodiments, a portion of the iontophoretic drug delivery system 700 is encoded with information indicative of a delivery device type (e.g., iontophoretic delivery device type, transdermal patch type, drug delivery device, and the like), a drug type, a dosing regimen, and the like. For example, in some embodiments, the information is encoded using one or more electrically resistive elements including, for example, one or more resistors, electrical traces, and the like.

In some embodiments, information is encoded using one or more electrical traces. A controller is operable to measure a resistance associated with the one or more electrical traces, and operable to correlate the measured resistance to at least one of a iontophoretic delivery device type, transdermal patch type, drug delivery device type, an active agent type, a delivery profile, and the like. In some embodiments, varying at least one of an electrical trace length, a trace width, a trace thickness, a trace material composition, the number of traces, and the like, can vary the resistance of the electrical trace. In some embodiments, a portion of the iontophoretic drug delivery system 700 is encoded with an electrically resistive element having an encoded resistance indicative of at least one of a iontophoretic delivery device type, transdermal patch type, drug delivery device type, an active agent type, a delivery profile, and the like.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety, including but not limited to: Japanese patent application Serial No. H03-86002, filed Mar. 27, 1991, having Japanese Publication No. H04-297277, issued on Mar. 3, 2000 as Japanese Patent No. 3040517; Japanese patent application Serial No. 11-033076, filed Feb. 10, 1999, having Japanese Publication No. 2000-229128; Japanese patent application Serial No. 11-033765, filed Feb. 12, 1999, having Japanese Publication No. 2000-229129; Japanese patent application Serial No. 11-041415, filed Feb. 19, 1999, having Japanese Publication No. 2000-237326; Japanese patent application Serial No. 11-041416, filed Feb. 19, 1999, having Japanese Publication No. 2000-237327; Japanese patent application Serial No. 11-042752, filed Feb. 22, 1999, having Japanese Publication No. 2000-237328; Japanese patent application Serial No. 11-042753, filed Feb. 22, 1999, having Japanese Publication No. 2000-237329; Japanese patent application Serial No. 11-099008, filed Apr. 6, 1999, having Japanese Publication No. 2000-288098; Japanese patent application Serial No. 11-099009, filed Apr. 6, 1999, having Japanese Publication No. 2000-288097; PCT patent application WO 2002JP4696, filed May 15, 2002, having PCT Publication No WO03037425; U.S. patent application Ser. No. 10/488,970, filed Aug. 24, 2004; Japanese patent application 2004/317317, filed Oct. 29, 2004; U.S. provisional patent application Ser. No. 60/627,952, filed Nov. 16, 2004; Japanese patent application Serial No. 2004-347814, filed Nov. 30, 2004; Japanese patent application Serial No. 2004-357313, filed Dec. 9, 2004; Japanese patent application Serial No. 2005-027748, filed Feb. 3, 2005; and Japanese patent application Serial No. 2005-081220, filed Mar. 22, 2005.

As one of skill in the art would readily appreciate, the present disclosure comprises methods of treating a subject by any of the compositions and/or methods described herein.

Aspects of the various embodiments can be modified, if necessary, to employ systems, circuits and concepts of the various patents, applications and publications to provide yet further embodiments, including those patents and applications identified herein. While some embodiments may include all of the membranes, reservoirs and other structures discussed above, other embodiments may omit some of the membranes, reservoirs, or other structures. Still other embodiments may employ additional ones of the membranes, reservoirs, and structures generally described above. Even further embodiments may omit some of the membranes, reservoirs and structures described above while employing additional ones of the membranes, reservoirs and structures generally described above.

These and other changes can be made in light of the above-detailed description. In general, in the following claims, the terms used should not be construed to be limiting to the specific embodiments disclosed in the specification and the claims, but should be construed to include all systems, devices and/or methods that operate in accordance with the claims. Accordingly, the invention is not limited by the disclosure, but instead its scope is to be determined entirely by the following claims.

What is claimed is:

1. A portable power supply system to provide power to an electrically powered device having at least two electrodes configured to provide an electrical potential therebetween and a set of at least two contacts accessible from an exterior of the electrically powered device and electrically coupleable to the at least two electrodes, the portable power supply system comprising:
   a power source including at least one cell selected from a group consisting of a chemical battery cell, an ultra-capacitor cell and a fuel cell; and
   a first magnetic coupling element coupled to the power source and that is magnetically-releasably attachable to the electrically powered device to retain the portable power supply system directly to the electrically powered device without the use of mechanical fasteners or adhesives such that at least two electrical contacts of the power source electrically conductively couple to respective ones of the at least two contacts of the electrically powered device to provide electrical power to power the electrically powered device in response to the portable power supply system being magnetically retained to the electrically powered device by the first magnetic coupling element.

2. The portable power supply system of claim 1 wherein the first magnetic coupling element takes the form of at least one ferrous metal element.

3. The portable power supply system of claim 1 wherein the first magnetic coupling element takes the form of at least one permanent magnet selected from the group consisting of a high-energy flexible magnet, a neodymium magnet, a ceramic magnet, a samarium cobalt magnet, or an alnico magnet.

4. The portable power supply system of claim 1, further comprising:
   a control circuit electrically coupled to receive a current from the power source and configured to control operation of the electrically powered device.

5. The portable power supply system of claim 4 wherein the control circuit is configured to automatically close in response to the portable power supply system being releasably attached to the electrically powered device.

6. The portable power supply system of claim 4 wherein the control circuit is operable to detect a power source polarity and provide a charge of a proper polarity to respective ones of a positive electrical contact and a negative electrical contact of the electrically powered device, in response to the portable power supply system being releasably attached to the electrically powered device.

7. The portable power supply system of claim 4 wherein the control circuit takes the form of a programmable control circuit operable to provide at least a first current profile to at least one of the electrodes of the electrically powered device.

8. The portable power supply system of claim 4 wherein the control circuit takes the form of a printed circuit on a substrate having at least a first side and a second side opposite to the first side, the first side having at least two electrical paths to provide electrical communication between the power source adjacent to the first side and at least two conductive paths on the second side, the at least two conductive paths on the second side configured to provide electrical communication between the portable power supply system and respective ones of the contacts of the electrically powered device.

9. The portable power supply system of claim 8, wherein the at least two conductive paths take the form of at least two conductive traces forming a generally concentric geometric pattern.

10. The portable power supply system of claim 1 further comprising:
a first one of the electrical contacts of the power source is electrically coupled to a first pole of the at least one cell; and
a second one of the electrical contacts of the power source is electrically coupled to a second pole of the at least one cell.

11. The portable power supply system of claim 10 wherein the first electrical contact is concentrically aligned with respect to the second electrical contact.

12. The portable power supply system of claim 11 wherein the first electrical contact is at least a portion of a circular conductive trace and the second electrical contact is at least a portion of a circular conductive trace.

13. The portable power supply system of claim 1, further comprising:
a second magnetic coupling element physically coupled to the power source, the second magnetic coupling element configured to releasably retain the portable power supply system in a correct electrical polarity with respect to the electrically powered device.

14. The portable power supply system of claim 1, further comprising:
a second magnetic coupling element physically coupled to the power source, the second magnetic coupling element having a magnetic polarity opposite a magnetic polarity of the first magnetic coupling element.

15. The portable power supply system of claim 1 wherein the at least one cell of the power source comprises at least one of a primary cell, a secondary cell, a button cell, a coin cell, an alkaline cell, a lithium cell, a lithium ion cell, a zinc air cell, or a nickel metal hydride cell.

16. The portable power supply system of claim 1 wherein the at least one cell of the power source comprises at least one of a printed battery, an energy cell laminate, a thin-film battery, or a power paper.

17. The portable power supply system of claim 1 wherein the portable power supply system is retained to the electrically powered device solely by magnetic attraction.

* * * * *